United States Patent
Young

(10) Patent No.: US 8,585,696 B2
(45) Date of Patent: Nov. 19, 2013

(54) ELECTROSURGICAL PROBE HAVING CONDUCTIVE OUTER SURFACE TO INITIATE ABLATION BETWEEN ELECTRODE

(75) Inventor: Kimbolt Young, Newtonville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 774 days.

(21) Appl. No.: 12/343,216

(22) Filed: Dec. 23, 2008

(65) Prior Publication Data
US 2009/0171340 A1    Jul. 2, 2009

Related U.S. Application Data

(60) Provisional application No. 61/017,444, filed on Dec. 28, 2007.

(51) Int. Cl.
*A61B 18/18*    (2006.01)
(52) U.S. Cl.
USPC ............... 606/41; 600/374; 600/384; 604/21; 604/528; 604/95.01; 604/95.04; 607/128
(58) Field of Classification Search
USPC ................. 600/374, 381; 604/21, 528, 95.01, 604/95.04; 606/41; 607/128
See application file for complete search history.

(56) References Cited

U.S. PATENT DOCUMENTS

| | | | |
|---|---|---|---|
| 5,010,894 A * | 4/1991 | Edhag | 607/128 |
| 5,239,999 A * | 8/1993 | Imran | 600/374 |
| 5,341,807 A * | 8/1994 | Nardella | 600/381 |
| 5,354,295 A | 10/1994 | Guglielmi et al. | |
| 5,383,852 A * | 1/1995 | Stevens-Wright | 604/95.04 |
| 5,401,239 A * | 3/1995 | Stephen et al. | 604/21 |
| 5,462,527 A * | 10/1995 | Stevens-Wright et al. | 604/528 |
| 5,611,777 A * | 3/1997 | Bowden et al. | 604/95.01 |
| 5,676,662 A | 10/1997 | Fleischhacker et al. | |
| 5,681,308 A * | 10/1997 | Edwards et al. | 606/41 |
| 5,810,802 A | 9/1998 | Panescu et al. | |
| 5,855,576 A | 1/1999 | LeVeen et al. | |
| 6,090,105 A | 7/2000 | Zepeda et al. | |
| 6,178,354 B1 * | 1/2001 | Gibson | 607/116 |
| 6,190,383 B1 | 2/2001 | Schmaltz et al. | |
| 6,312,428 B1 | 11/2001 | Eggers et al. | |
| 6,315,778 B1 * | 11/2001 | Gambale et al. | 606/41 |
| 6,337,998 B1 | 1/2002 | Behl et al. | |
| 6,502,576 B1 * | 1/2003 | Lesh | 128/898 |

(Continued)

OTHER PUBLICATIONS

Bipolar Electrosurgical Probe Having Insulated Overlapping Conductive elements, U.S. Appl. No. 12/262,073, filed Oct. 30, 2008, Inventor: Kimbolt Young.

(Continued)

*Primary Examiner* — Theodore J Stigell
*Assistant Examiner* — Scott Medway
(74) *Attorney, Agent, or Firm* — Bingham McCutchen LLP

(57) ABSTRACT

Tissue ablation probes and methods of treating diseased tissue are disclosed that include or use a partially uninsulated shaft that carries conductive elements such as electrode arrays. The shaft has an uninsulated outer surface that is electrically conductive and is electrically connected to one of the conductive elements. The uninsulated outer surface and one of the conductive elements are insulated from the other conductive element. Tissue ablation is performed "inside-out" and begins between the proximal and distal electrode arrays and migrates outwardly towards the electrode arrays when electrical current is applied to the probe.

14 Claims, 31 Drawing Sheets

(56) References Cited

U.S. PATENT DOCUMENTS

| | | | |
|---|---|---|---|
| 6,514,246 | B1 | 2/2003 | Swanson et al. |
| 6,616,655 | B1* | 9/2003 | Falwell et al. ............ 606/41 |
| 6,837,886 | B2* | 1/2005 | Collins et al. ............ 606/41 |
| 7,108,696 | B2 | 9/2006 | Daniel et al. |
| 7,195,629 | B2 | 3/2007 | Behl et al. |
| 7,387,628 | B1 | 6/2008 | Behl et al. |
| 7,416,549 | B2 | 8/2008 | Young et al. |
| 7,517,349 | B2 | 4/2009 | Truckai et al. |
| 7,846,157 | B2* | 12/2010 | Kozel ............ 606/41 |
| 2002/0107511 | A1* | 8/2002 | Collins et al. ............ 606/41 |
| 2004/0158239 | A1 | 8/2004 | Behl et al. |
| 2005/0080409 | A1* | 4/2005 | Young et al. ............ 606/41 |
| 2005/0256521 | A1* | 11/2005 | Kozel ............ 606/41 |
| 2005/0288663 | A1 | 12/2005 | Behzadian |
| 2006/0089635 | A1 | 4/2006 | Young et al. |
| 2006/0149226 | A1 | 7/2006 | McCullagh et al. |
| 2006/0167448 | A1 | 7/2006 | Kozel |
| 2006/0287650 | A1 | 12/2006 | Cao et al. |
| 2009/0118731 | A1 | 5/2009 | Young et al. |
| 2009/0306549 | A1* | 12/2009 | MacAdam et al. ............ 601/2 |

OTHER PUBLICATIONS

PCT International Search Report for PCT/US2008/088213, Applicant: Boston Scientific Scimed, Inc., Form PCT/ISA/210 and 220, dated Apr. 20, 2009 (8 pages).

PCT Written Opinion of the International Search Authority for PCT/US2008/088213, Applicant: Boston Scientific Scimed, Inc., Form PCT/ISA/237, dated Apr. 20, 2009 (8 pages).

PCT International Search Report for PCT/US2008/088226, Applicant: Boston Scientific Scimed, Inc., Form PCT/ISA/210 and 220, dated Apr. 6, 2009 (7 pages).

PCT Written Opinion of the International Search Authority for PCT/US2008/088226, Applicant: Boston Scientific Scimed, Inc., Form PCT/ISA/237, dated Apr. 6, 2009 (7 pages).

PCT International Preliminary Report on Patentability (Chapter I of the Patent Cooperation Treaty) for PCT/US2008/088226, Applicant: Boston Scientific Scimed, Inc., Form PCT/IB/326 and 373, dated Jul. 8, 2010 (9 pages).

PCT International Preliminary Report on Patentability (Chapter I of the Patent Cooperation Treaty) for PCT/US2008/088213, Applicant: Boston Scientific Scimed, Inc., Form PCT/IB/326 and 373, dated Jul. 8, 2010 (8 pages).

Office Action dated Aug. 3, 2011 in U.S. Appl. No. 12/343,150, filed Dec. 23, 2008, inventor: Kimbolt Young, 17 pages.

File History of U.S. Appl. No. 12/343,150, inventor: Kimbolt Young, filed Dec. 23, 2008.

Office Action dated Mar. 26, 2012 in U.S. Appl. No. 12/343,150, filed Dec. 23, 2008, inventor: Kimbolt Young, (7 pages).

Office Action dated Aug. 29, 2012 in U.S. Appl. No. 12/343,150, filed Dec. 23, 2008, inventor: Kimbolt Young, (11 pages).

Office Action dated Dec. 10, 2012 in U.S. Appl. No. 12/343,150, filed Dec. 23, 2008, inventor: Kimbolt Young, (9 pages).

* cited by examiner

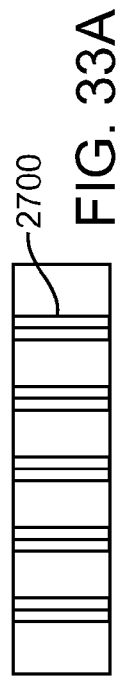
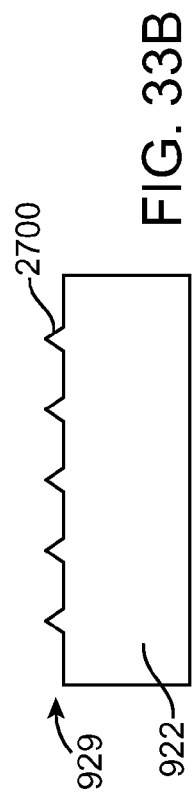
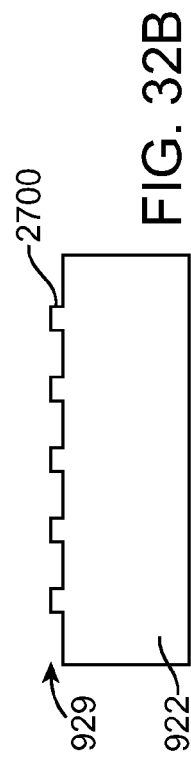
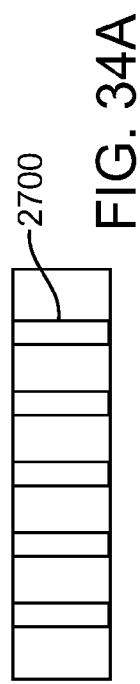
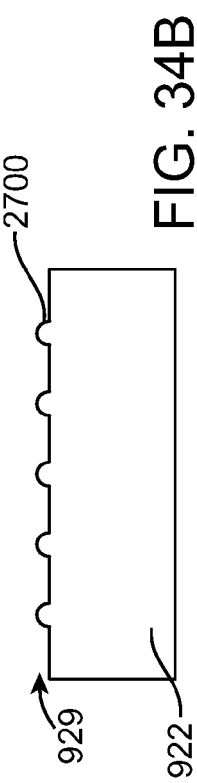

ELECTROSURGICAL PROBE HAVING CONDUCTIVE OUTER SURFACE TO INITIATE ABLATION BETWEEN ELECTRODE

RELATED APPLICATION

This Application claims priority to U.S. Provisional Patent Application No. 61/017,444 filed on Dec. 28, 2007. The above-noted U.S. Provisional Patent Application is incorporated by reference as if set forth fully herein.

FIELD OF INVENTION

The present invention relates to electrosurgical devices.

BACKGROUND

Electrosurgery is a widely used surgical procedure for treating tissue abnormalities. For example, it is known to use radio frequency (RF) energy to treat or ablate cancerous lesions in the liver, kidney, lungs and other tissues. RF ablation occurs as a result of a high frequency alternating current (AC) flowing from the tip of an electrode through the surrounding tissue. Ionic agitation is produced in the tissue around the electrode tip as the ions attempt to follow the change in direction of the alternating current. This ionic agitation creates frictional heating and necrosis of the tissue around the electrode. Such procedures may be performed through an open abdominal incision or via laparoscopy, which is performed through multiple, small skin incisions, and can also be conducted percutaneously.

Electrosurgical devices that can be used for tissue ablation using RF energy generally fall into one of two categories, monopolar devices and bipolar devices. Monopolar electrosurgical devices typically include an electrosurgical probe having a first or "active" electrode extending from one end. The electrosurgical probe is electrically coupled to an electrosurgical generator, such as a RF generator, which provides a high frequency electrical current. During an operation, a second or "return" electrode, having a much larger surface area than the active electrode, is positioned in contact with the skin of the patient. The surgeon may then bring the active electrode in close proximity to the tissue and activate a switch, causing electrical current to flow from the distal portion of the active electrode and through tissue to the larger return electrode.

Bipolar electrosurgical devices do not use a return electrode. Instead, bipolar devices include a second electrode that is positioned adjacent to the first electrode. Both electrodes are attached to an electrosurgical probe. As with monopolar devices, the bipolar electrosurgical probe is electrically coupled to an electrosurgical generator. When the generator is activated, electrical current flows from the end of the first electrode through intervening tissue to the end of the adjacent second electrode.

Referring to FIGS. 1 and 2, one known bipolar electrosurgical probe 10 includes a shaft or cannula 20 that includes a proximal shaft, cannula or conductive element 22 (generally referred to as a proximal cannula) and a distal shaft portion, cannula or conductive element 24 (generally referred to as a distal cannula). An insulative member 26 separates and electrically isolates the proximal and distal cannulas 22 and 24. The outer surface of the shaft 20 includes an insulative coating 28. The proximal cannula 22 is electrically isolated from the distal array 34, and the distal cannula 24 is electrically isolated from the proximal array 32.

Referring to FIGS. 1 and 3, individual electrodes of the proximal and distal electrode arrays 32 and 34 are initially retained inside the shaft 20. During use, the distal end of the shaft 20 is inserted into diseased tissue, and individual electrodes 36 of the proximal electrode array 32 are deployed through ports 42 defined by a proximal cannula 22, and individual electrodes 38 of the distal electrode array 34 are deployed through ports 44 defined by the distal cannula 24. Deployment is performed using one or more reciprocating shafts or other components, e.g., as described in U.S. Publication No. 2005/0080409, the contents of which are incorporated herein by reference.

In the illustrated device, the deployed electrode arrays 32 and 34 face each other. This arrangement is referred to as a symmetric or mirrored arrangement since a balanced current density exists between the two electrode arrays 32 and 34. More particularly, referring to FIG. 3, electrical current flows between an active array (+) 34 and a return array (−) 32. Ablation regions or lesions 52 and 54 (generally referred to as an ablation lesion) initially form around the tips of the individual electrodes 36 and 38.

With continued application of current, ablation lesions 52 and 54 symmetrically grow inwardly and eventually meet in a middle region between the electrode arrays 32 and 34 to ablate the middle portion of diseased tissue. Symmetrically configured probes that operate in this manner are otherwise described as probes that perform ablation in an "outside-in" manner.

Referring to FIG. 4, it is also known to use bipolar electrosurgical probes 60 that are asymmetric in that the proximal and distal arrays 32 and 34 face the same direction, and there is an unbalanced current density and unbalanced formation of ablation lesions between the electrode arrays 32 and 34. More particularly, referring to FIG. 5, electrical current (represented as arrows) flows between an active electrode array (+) 34 and a return electrode array (−) 32.

Referring to FIG. 6, an ablation lesion 72 initially forms around an arcuate surface of electrodes 36 of the proximal electrode array 32, and other, smaller ablation lesions 74 form around the distal tips of individual electrodes 38 of the distal electrode array 34. As shown in FIG. 6, the resulting ablation is unbalanced and biased around the proximal electrode array 32 as a result of low current density along the shaft 20 (generally illustrated in FIG. 8), and the larger surface area of the electrode array 32 compared to the tips of the electrodes 38 of the distal electrode array 34. Thus, ablation around the distal electrode array 34 lags behind ablation around the proximal electrode array 32. Referring to FIG. 7, as additional current is applied to the probe 60, over time, the ablation lesion 72 and the smaller ablation lesions 74 grow and eventually fill in the space between the electrode arrays 32 and 34 until the ablation lesions 72 and 74 meet in a middle region.

Thus, similar to the ablation probe 10 shown in FIGS. 1 and 3 having electrode arrays 32 and 34 that face the same direction, probes 60 shown in FIGS. 4-7 having arrays 32 and 34 that face different directions may also initially form ablation lesions around the outer electrode arrays 32 and 34, which grow and migrate inwardly toward the center or a middle region between the electrode arrays 32 and 34.

Uneven ablation patterns may result in an "hour glass" shaped lesion due to ablation migrating inwardly from the outer electrodes and towards the middle region. The middle region of diseased tissue, which is often the bulk of the tissue to be treated, may be only partially ablated or not ablated at all. This may be common if the procedure is interrupted.

Other known probes include electrode arrays that face opposite directions (symmetrical configuration) and include an additional electrode array to boost the ablation in the middle region. Such probes may improve upon hour glass ablation patterns, but they also use additional electrode arrays and involve more complicated structural configurations in order to connect, insulate and deploy the array components.

Probes having electrode arrays facing the same direction (asymmetrical configuration) also exhibit "hour glass" ablation patterns. Further, such probes typically involve longer ablation times for the middle region of diseased tissue to be ablated. Accordingly, it would be desirable to have electrosurgical probes that are able to form larger and more complete ablation lesions in less time. Further, it would be desirable to reduce or eliminate "hour glass" shaped lesions.

SUMMARY

According to one embodiment, a tissue ablation probe includes a proximal electrically conductive element, a distal electrically conductive element and a shaft that carries the electrically conductive elements. The shaft includes an uninsulated outer surface that is located between the proximal and distal conductive elements. The uninsulated outer surface is electrically connected to one of the conductive elements, and the electrically connected uninsulated outer surface and conductive element are electrically insulated from the other conductive element.

According to a further embodiment, a tissue ablation probe includes proximal and distal electrode arrays and a shaft that carries the electrode arrays. The shaft includes an uninsulated outer surface that located between the electrode arrays. The uninsulated outer surface is electrically connected to one of the electrode arrays, and the electrically connected uninsulated outer surface and electrode array are insulated from the other electrode array.

According to another embodiment, a tissue ablation probe includes proximal and distal electrode arrays, electrically insulated proximal and distal cannulas, and a shaft. The proximal cannula carries the proximal electrode array, and the distal cannula carries the distal electrode array. One of the cannulas has an electrically conductive, uninsulated outer surface that is located between the electrode arrays. The uninsulated outer surface and one of the electrode arrays are electrically connected together. The electrically connected uninsulated outer surface and electrode array are insulated from the other electrode array. The probe components are configured so that tissue ablation can be initiated in a region adjacent the uninsulated outer surface and between the proximal and distal electrode arrays when electrical current is conveyed to the probe.

According to another alternative embodiment, a bipolar tissue ablation probe includes proximal and distal arrays that face the same direction and a partially insulated shaft that carries the electrode arrays. Each electrode array includes a plurality of electrodes that can assume retracted and deployed configurations. The shaft includes proximal and distal cannulas, each of which defines one or more apertures and carries respective electrode arrays. One cannula, such as the distal cannula, has an electrically conductive, uninsulated outer surface that is located between the electrode arrays. The uninsulated outer surface is electrically connected to one of the electrode arrays, and the electrically connected uninsulated outer surface and electrode array are insulated from the other electrode array. Further, an insulative member electrically isolates the proximal and distal cannulas. The electrodes of the arrays can move axially from an initial retracted position and then evert from the initial retracted position to a deployed configuration as the individual electrodes are deployed through respective apertures defined by respective cannulas. The probe components are configured so that tissue ablation begins in a region between the electrode arrays and adjacent to the uninsulated outer surface of the distal cannula when electrical current is conveyed to the probe.

A further embodiment is directed to a method of treating tissue having a diseased region, such as a tumor. The method includes initially placing a probe having a shaft that carries first and second electrically conductive elements in contact with the diseased region and that includes an uninsulated outer surface, which is electrically connected to one of the electrically conductive elements. The method also includes conveying electrical current between the uninsulated outer surface and the one of the electrically conductive elements, and conveying electrical current between the first and second electrically conductive elements. Ablation of the diseased region can be initiated between the conductive elements and continue around the conductive elements.

Another embodiment is directed to a method of treating tissue having a diseased region, such as a tumor, and includes initially placing a probe in contact with the diseased region, the probe having a shaft including proximal and distal cannulas carrying respective electrode arrays and an uninsulated outer surface located between the arrays. The uninsulated outer surface is electrically connected to one of the electrode arrays. The method further includes conveying electrical current between the uninsulated outer surface and one of the electrode arrays, and conveying electrical current between the electrode arrays. Ablation of the diseased region can be initiated between the electrode arrays and continue around the first and second electrode arrays.

In a further alternative embodiment, a method of treating tissue having a diseased region, such as a tumor, includes initially placing a probe in contact with the diseased region. The probe includes shaft having proximal and distal cannulas carrying respective electrode arrays and uninsulated outer surface that is located between the arrays. The uninsulated outer surface is electrically connected to one of the arrays. The method also includes deploying electrodes of the electrode arrays from respective proximal and distal cannulas, conveying electrical current between the uninsulated outer surface and one of the arrays, and conveying electrical current between the arrays. Ablation of the diseased region can be initiated between the electrode arrays and continue around the first and second electrode arrays.

In one or more embodiments, tissue ablation begins in a region between the proximal and distal electrode arrays when electrical current is conveyed to the probe, e.g., adjacent to the uninsulated outer surface. Tissue ablation can then simultaneously migrate outwardly towards the proximal and distal conductive elements or electrode arrays.

In one or more embodiments, the uninsulated surface is electrically connected to the distal conductive element or distal electrode array. For example, the uninsulated outer surface can be an uninsulated outer surface of a distal cannula that carries a distal conductive element or distal electrode array. Thus, when electrical current is applied to the probe, the uninsulated outer surface and the distal electrode array are the same polarity.

In embodiments including electrode arrays, each array includes a plurality of electrodes that can initially move axially and then evert as they are deployed through apertures defined by the shaft.

In one or more embodiments, the proximal and distal conductive elements or electrode arrays face the same direction and are part of a bipolar tissue ablation probe.

Other aspects of embodiments are described herein and will become apparent upon reading the following detailed description with reference to the accompanying drawings.

BRIEF DESCRIPTION OF THE DRAWINGS

Referring now to the drawings in which like reference numbers represent corresponding parts throughout and in which:

FIG. 32A is a top view of an uninsulated outer surface of a shaft having a plurality of current enhancing protrusions in the form of ridges extending circumferentially around the uninsulated outer surface according to one embodiment;

FIG. 32B is a side view of FIG. 32A;

FIG. 33A is a top view of an uninsulated outer surface of a shaft having a plurality of current enhancing protrusions in the form of edges or pointed ridges extending circumferentially around the uninsulated outer surface according to another embodiment;

FIG. 33B is a side view of FIG. 33A;

FIG. 34A is a top view of an uninsulated outer surface of a shaft having a plurality of current enhancing protrusions in the form of rounded ridges extending circumferentially around the uninsulated outer surface according to a further embodiment;

FIG. 34B is a side view of FIG. 34A;

DETAILED DESCRIPTION OF ILLUSTRATED EMBODIMENTS

The illustrated embodiments provide electrosurgical probes with improved ablation patterns and capabilities that advantageously achieve more complete ablation in less time compared to known probes. The illustrated embodiments also advantageously initiate formation of ablation lesions in a middle region of diseased tissue, e.g., between proximal and distal electrode elements, such as electrode arrays. Ablation lesions grow outwardly towards electrode arrays so that ablation is performed "inside-out" rather than "outside-in" to reduce or eliminate "hour glass" ablation shapes. The illustrated embodiments achieve these advantages in a manner that is less complex than other probes that are used to address hour glass lesion shapes since the embodiments do not require additional electrode arrays and the associated additional conductive and insulative components.

Further advantages of embodiments include increasing current density and ablation capabilities through the use of current enhancing protrusions or surface modifications, such as one or more edges or focal points, which serve to increase current density along selected portions of a probe and to bias and/or enhance ablation. Protrusions can be attached to, formed on or defined by the shaft of the probe between electrode arrays and/or on individual electrodes of electrode arrays to controllably bias formation and growth of ablation lesions. Aspects of illustrated embodiments are described in further detail with reference to FIGS. 9-42.

Figure 1:
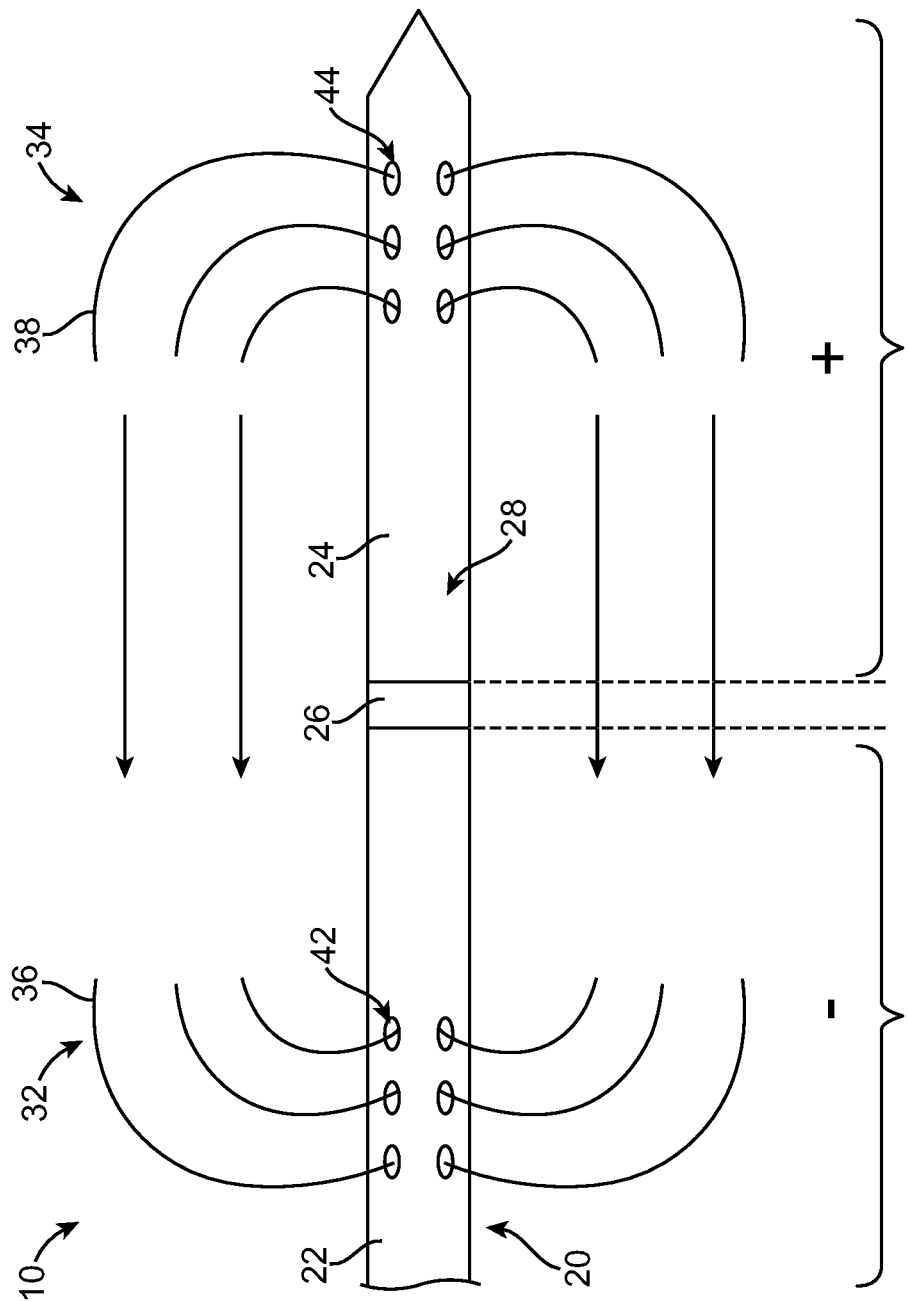
FIG. 1 illustrates a known symmetrical bipolar ablation probe having electrode arrays that face each other.
Figure 2:
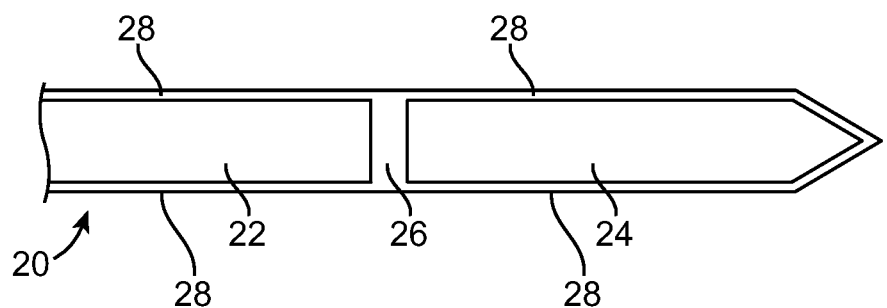
FIG. 2 further illustrates a shaft or cannula of a known ablation probe.
Figure 3:
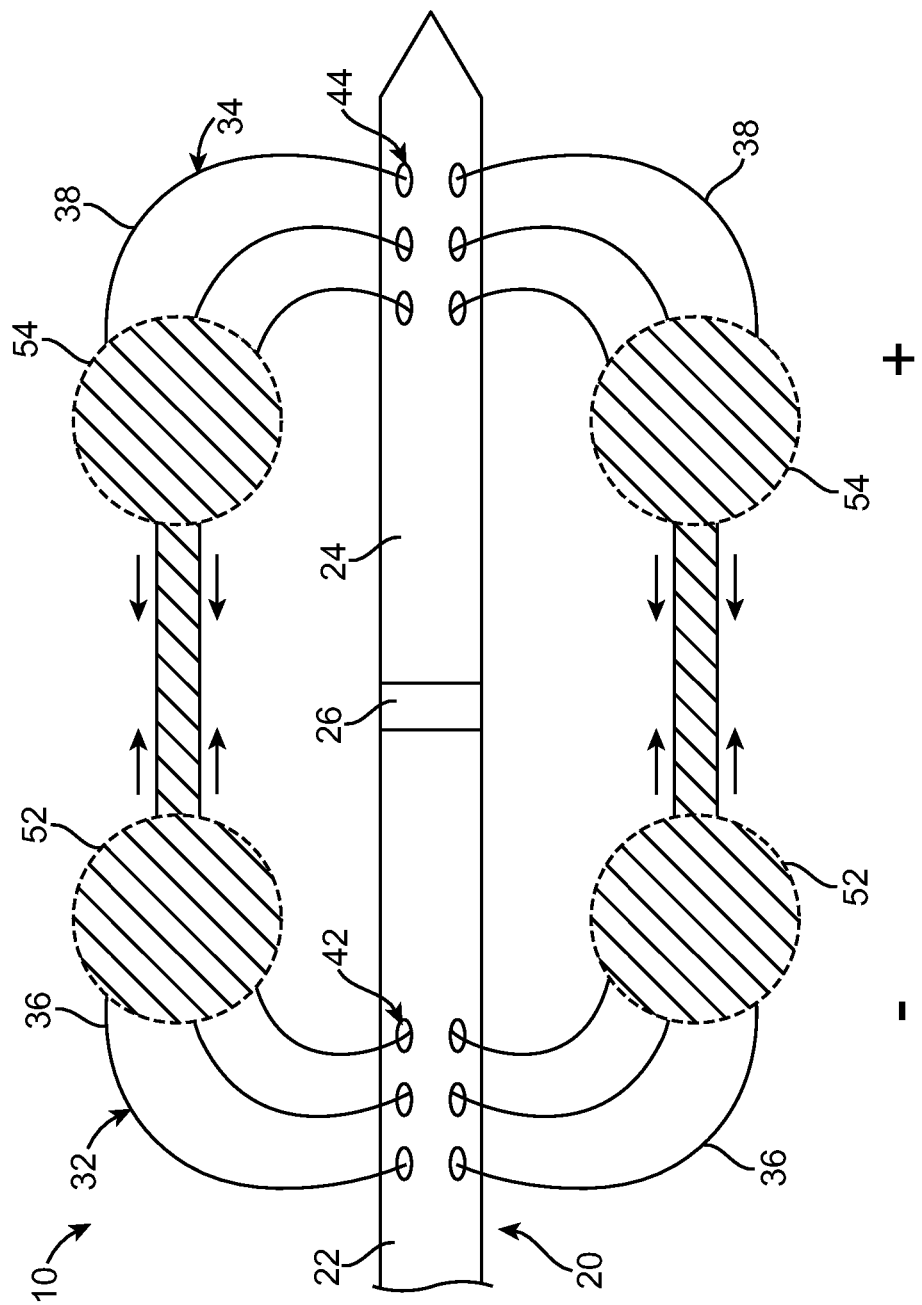
FIG. 3 illustrates formation of ablation lesions using a known symmetrical bipolar ablation probe.
Figure 4:
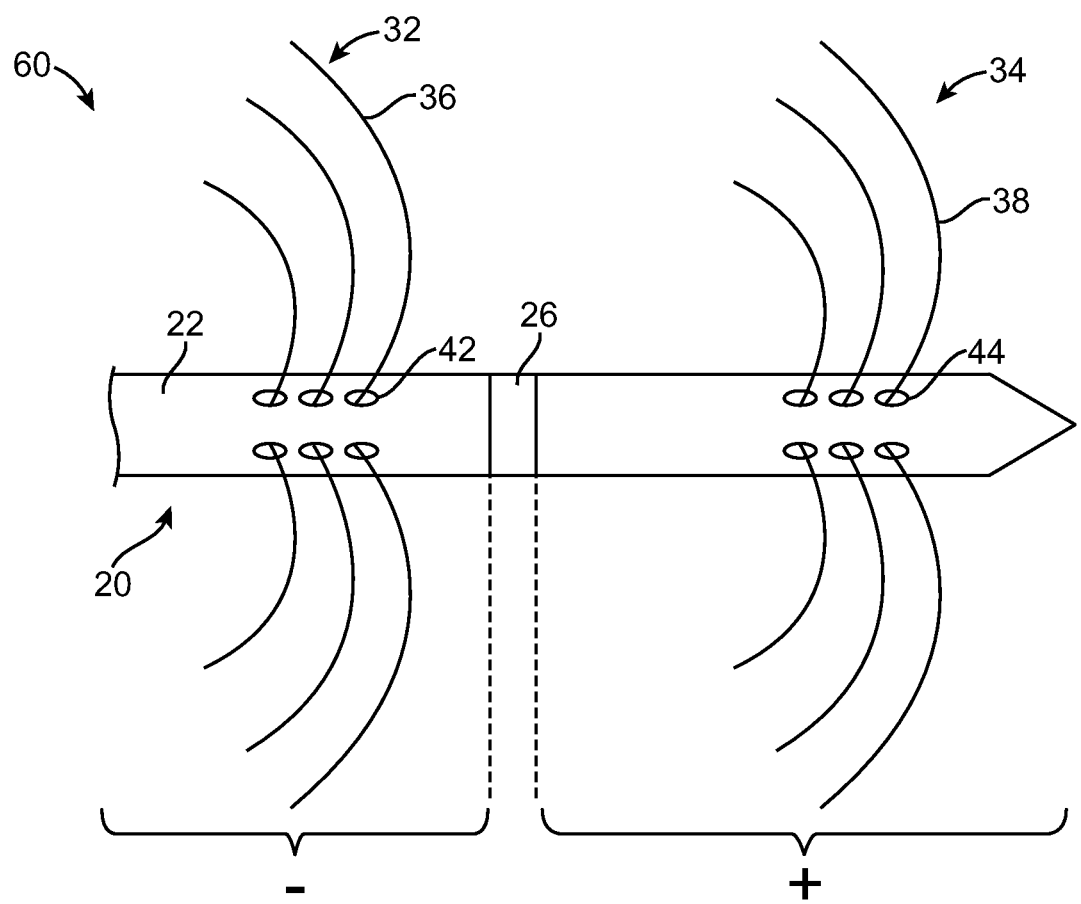
FIG. 4 illustrates a known asymmetrical bipolar ablation probe having electrode arrays that face the same direction.
Figure 5:
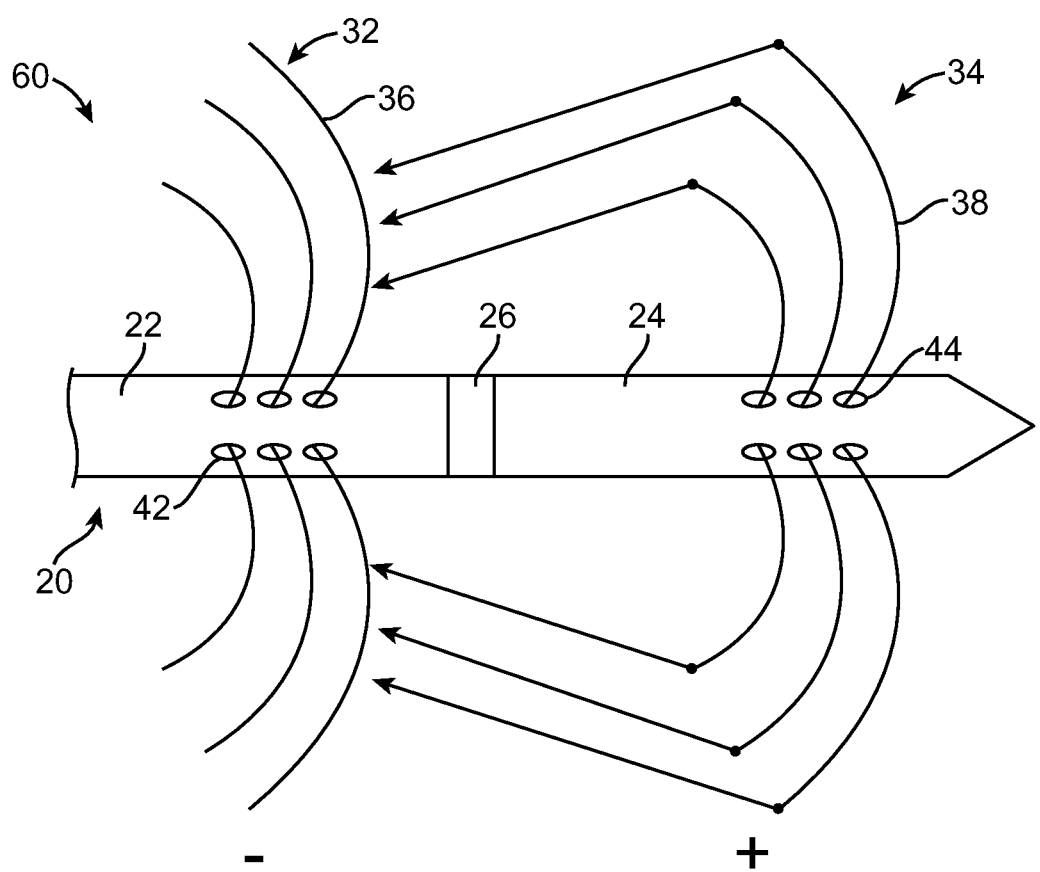
FIG. 5 illustrates current paths between electrode arrays of an asymmetrical bipolar ablation probe.
Figure 6:
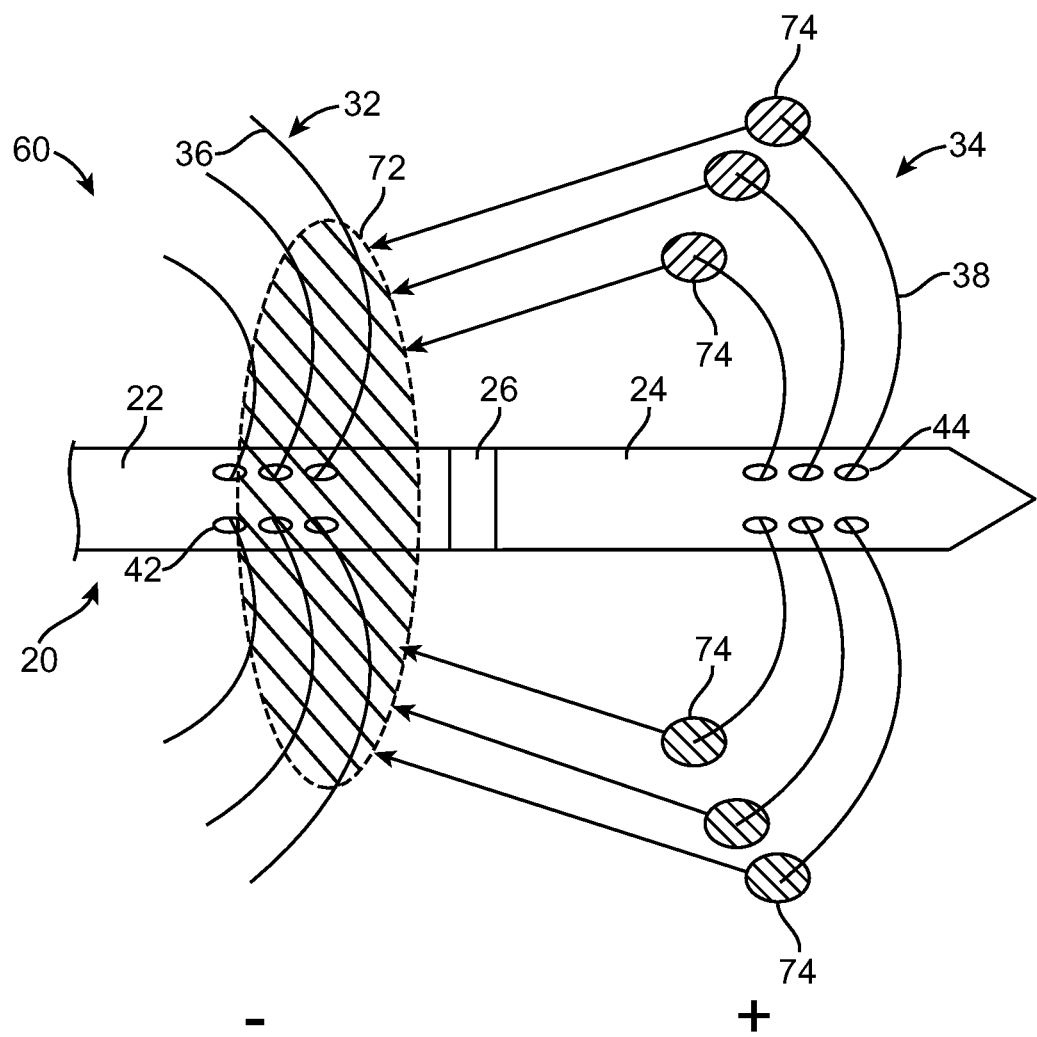
FIG. 6 illustrates formation of unbalanced ablation lesions using a known asymmetrical bipolar ablation probe.
Figure 7:
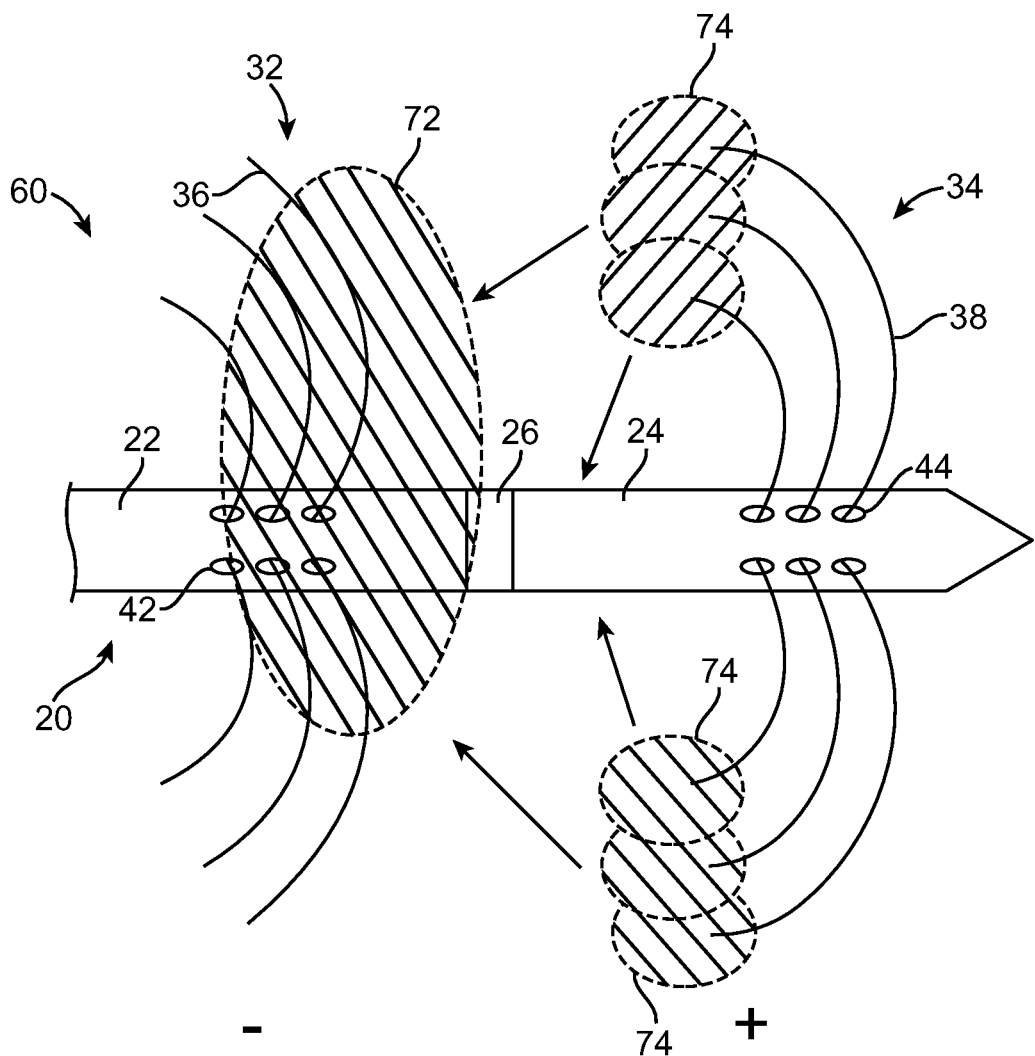
FIG. 7 further illustrates formation of unbalanced ablation lesions using a known asymmetrical bipolar ablation probe.
Figure 8:
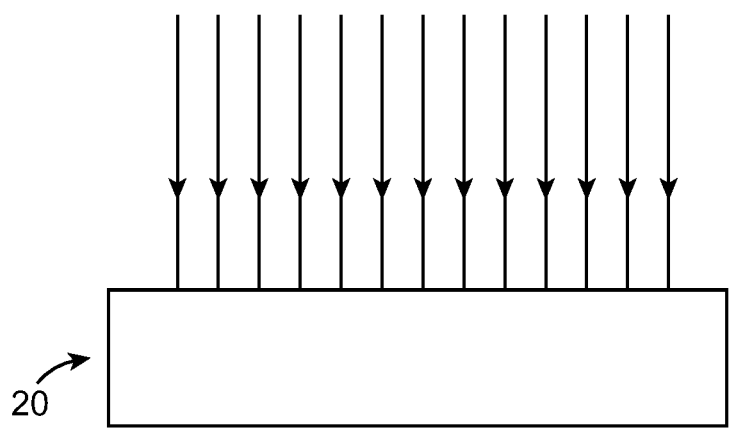
FIG. 8 generally illustrates low current density on a shaft of a known bipolar asymmetrical ablation probe.
Figure 9:
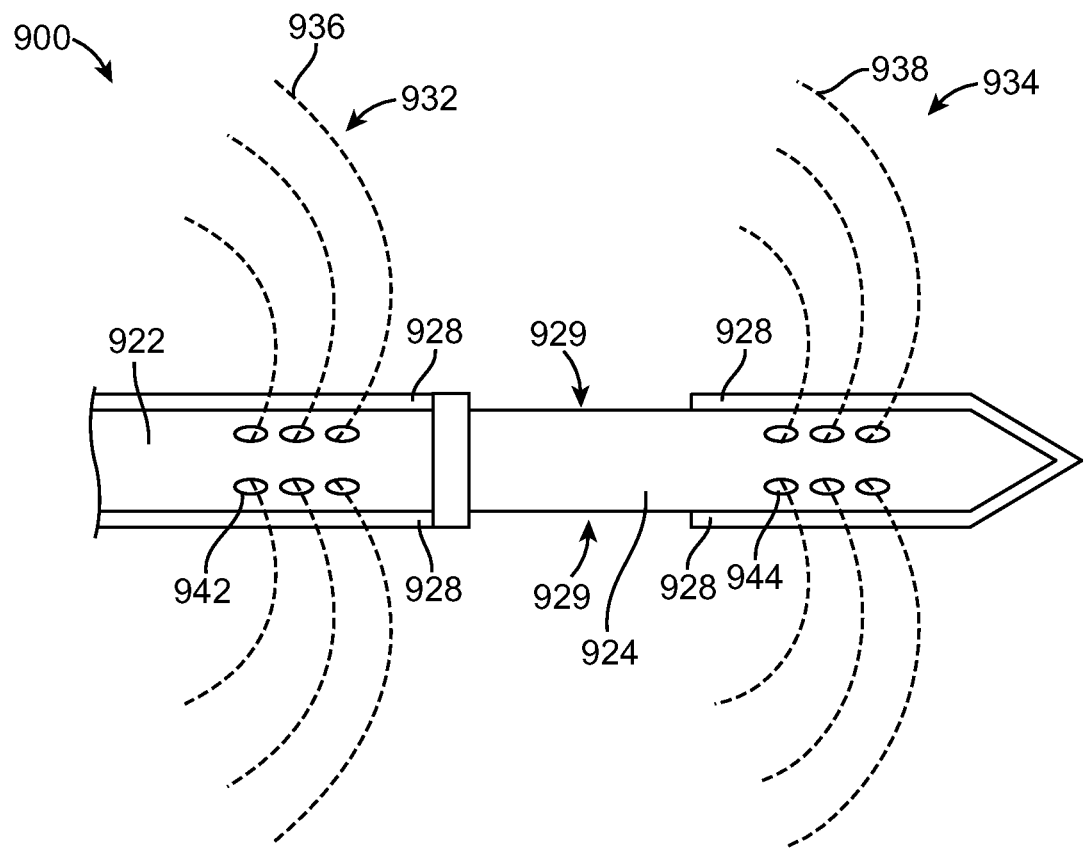
FIG. 9 illustrates an ablation probe having an uninsulated, conductive outer surface according to one embodiment.
Figure 10:
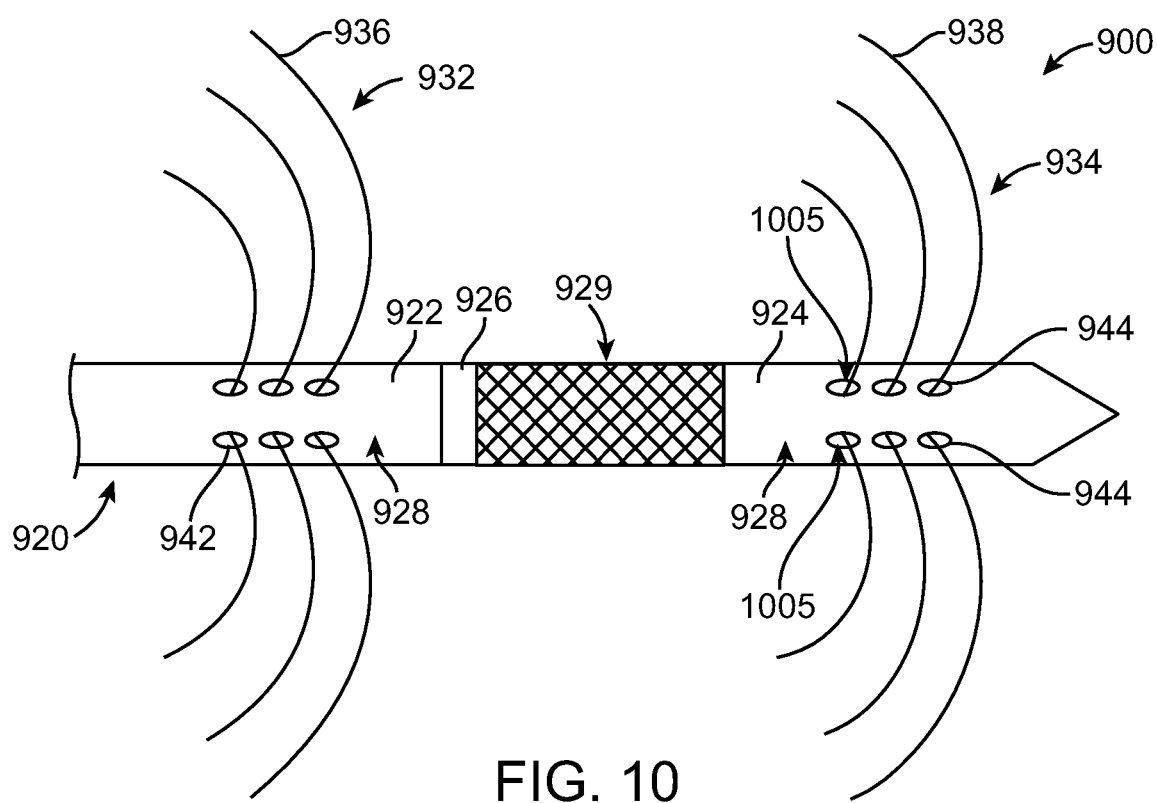
FIG. 10 further illustrates an ablation probe having an uninsulated, conductive outer surface according to one embodiment.

Referring to FIGS. 9 and 10, according to one embodiment, an electrosurgical probe 900 includes a partially insulated shaft 920 that carries a first or proximal electrode, e.g., an electrode array 932 (shown in phantom lines representing a retracted position) and a second or distal electrode, e.g., electrode array 934 (also shown in phantom lines representing a retracted position). In the illustrated embodiment, the shaft 920 includes a first or proximal cannula or first electrically conductive elements 922 (generally referred to as a proximal cannula 922), a second or distal cannula or second electrically conductive element 924 (generally referred to as a distal cannula 924), and an insulation or non-conductive member 926 that separates and electrically isolates the proximal and distal cannulas 922 and 924. The shaft 920 also includes an insulative coating or covering 928.

The shaft 920 is partially insulated since one or more surfaces or regions 929 of the shaft 920 do not include the insulative coating 928. One or more surfaces of a cannula are uninsulated and electrically connected to an electrode, such as an electrode array. In one embodiment, an outer surface of the distal cannula 924 is the uninsulated outer surface or region 929 and is electrically conductive and electrically connected to the distal electrode array 934. Alternatively, an outer surface of a proximal cannula 922 can be the uninsulated outer surface or region 929, which is electrically connected to the proximal array. For purposes of explanation and illustration, this specification describes a distal cannula 924 having an uninsulated outer surface 929 that is electrically connected to a distal electrode array 934. The exposed outer surface 929 of the distal cannula 924 is represented by cross-hatching in FIG. 10. The uninsulated outer portion 929 can, for example, be formed by removing a portion of the insulative coating 928.

In the embodiment illustrated in FIG. 10, the probe 900 includes an uninsulated outer surface or region 929 (generally "uninsulated outer surface 929") that is adjacent to the insulative member 926 that electrically isolates the proximal and distal cannulas 922 and 924. In other embodiments, the uninsulated outer surface 929 may or may not be adjacent to the insulative member 926. For example, an outer surface of the distal cannula 924 having an outer coating 928 may be positioned between the insulative member 926 and an uninsulated outer surface 929.

FIG. 10 illustrates a deployed first or proximal electrode array 932 that includes individual needles or electrodes 936 that extend through apertures or ports 942 defined by the proximal cannula 922. Similarly, a second or distal electrode array 934 includes individual needles or electrodes 938 that extend through apertures or ports 944 defined by the distal cannula 924.

In one embodiment, a distal mandrel or inner shaft (not shown in FIG. 10) seated within the shaft 920 carries the distal electrode array 934 and is electrically connected to the uninsulated outer surface 929 of the distal cannula 924. Thus, application of electrical current to the distal mandrel or inner shaft results in application of electrical current to the uninsulated outer surface 929. In another embodiment, the distal mandrel or inner shaft that carries the distal electrode array 934 is electrically connected to the uninsulated outer surface 929 of the distal cannula 924 when electrodes 938 are deployed. More specifically, when deployed, the electrodes 938 contact the outer surface of the distal cannula 924, identified as electrical connection 1005.

Figure 11:
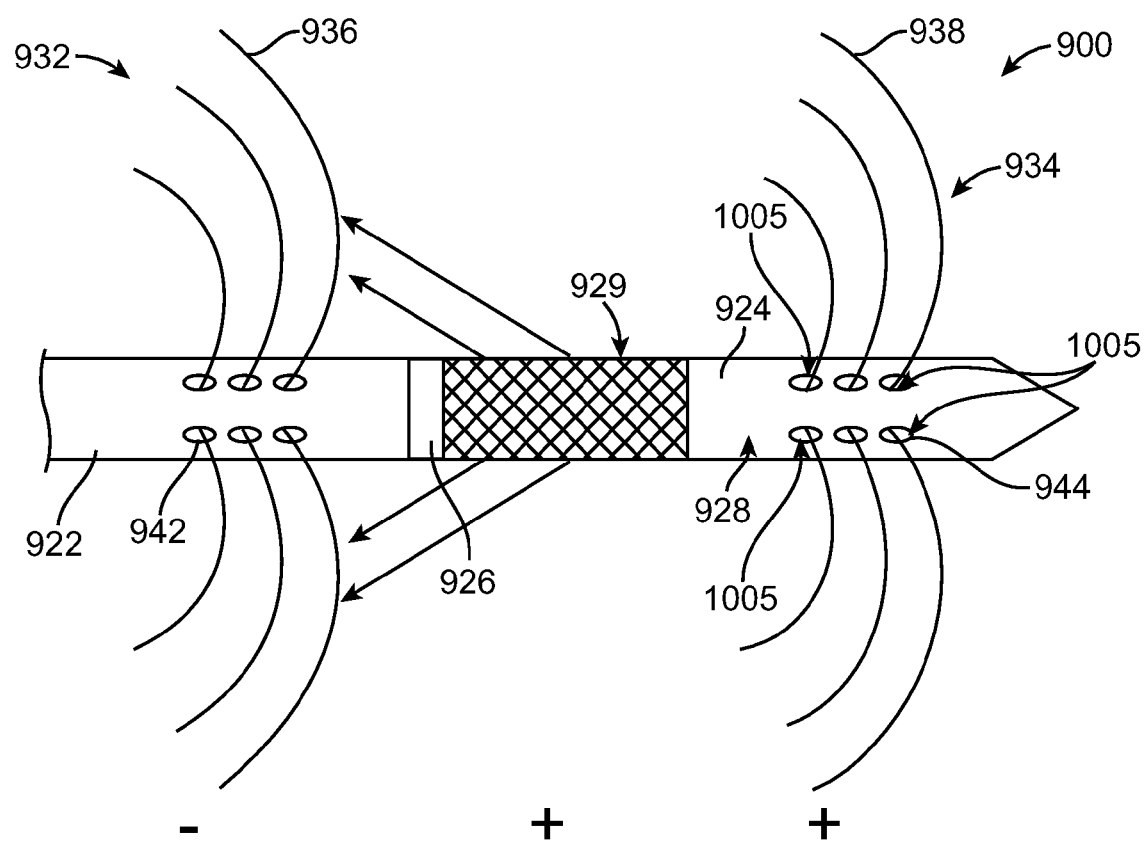
FIG. 11 illustrates polarities of different parts of a probe and a current path between an uninsulated outer surface and a proximal electrode array according to one embodiment.

FIG. 11 further illustrates the uninsulated outer surface 929 and the electrode array 934 being electrically connected (by a selected suitable manner) and being the same polarity when electrical current is conveyed to the probe 900. In the illustrated embodiment, the uninsulated outer surface 929 of the first cannula 924 and the first electrode array 934 are electrically connected and have a positive (+) polarity. The uninsulated outer surface 929 and the distal electrode array 934 are electrically insulated from the proximal electrode array 932, shown as having negative (−) polarity.

Electrical current flows from a positive (+) polarity surface to the return proximal array (−). In the illustrated embodiment, since the uninsulated outer surface 929 (+) is the positive polarity surface that is closest to the negative polarity surface of the proximal array 932 (−), electrical current will initially flow between the uninsulated outer surface 929 (+) and the outer arcuate surfaces of the electrodes 936 of the proximal electrode array 932 (−), as shown by current direction arrows in FIG. 11. The current flow results in formation of an ablation lesion between respective proximal and distal electrode arrays 932 and 934. With this configuration, ablation lesions grow "inside out" rather than "outside-in." Formation and growth of middle ablation regions between the electrode arrays 932 and 934 according to embodiments are further illustrated with reference to FIGS. 12-19.

Figure 12:
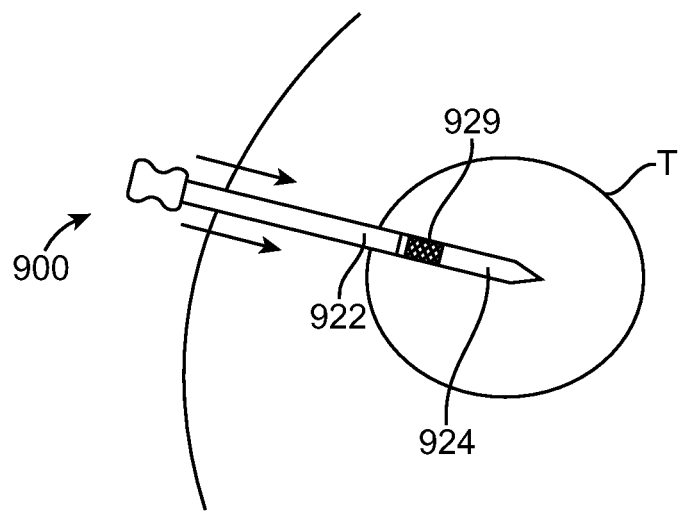
FIG. 12 illustrates an ablation probe according to one embodiment inserted within tissue to be treated.

Referring to FIG. 12, a probe assembly, such as probe 900, is configured for introduction into the body of a patient for ablative treatment of target or diseased tissue (T). Embodiments can be used to treat tissues including liver, kidney, pancreas, breast, prostrate (not accessed via the urethra), and the like. The treatment region may be identified using conventional imaging techniques capable of elucidating a target tissue (T), e.g., tumor tissue, such as ultrasonic scanning, magnetic resonance imaging (MRI), computer-assisted tomography (CAT), fluoroscopy, nuclear scanning (using radio-labeled tumor-specific probes), and the like. Probe assembly components may be made of suitable materials that are compatible with different imaging systems and techniques. The probe 900 can be accomplished using any one of a variety of techniques, including percutaneously directly through the patient's skin or through an open surgical incision. In this case, the distal cannula 924 may have a sharpened tip, e.g., in the form of a needle (as shown in various figures), to facilitate introduction to the treatment region. In such cases, it is desirable that the shaft 920 be sufficiently rigid, i.e., has sufficient column strength, so that it can be accurately advanced through tissue T. In other cases, the shaft 920 may relatively flexible if other introduction devices and methods are utilized.

Figure 13:
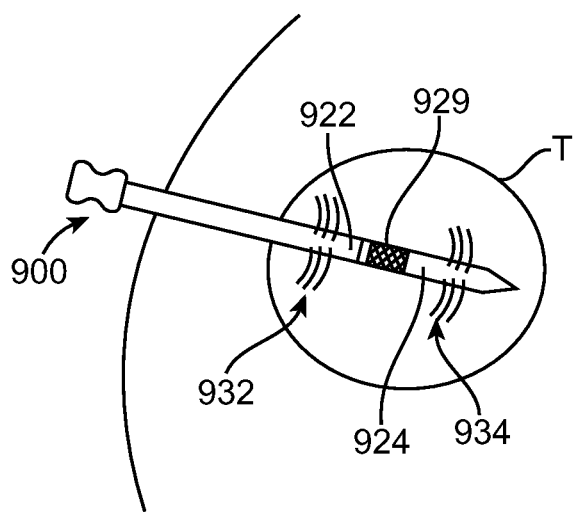
FIG. 13 illustrates an ablation probe according to one embodiment inserted within tissue to be treated following deployment of electrode arrays.

Referring to FIG. 13, after the probe 900 is properly positioned inside the target tissue (T), the proximal and distal arrays 932 and 934 can be deployed through respective ports 942 and 944 of respective proximal and distal cannulas 922 and 924 so that they are positioned inside the diseased tissue (T)

Figure 14:
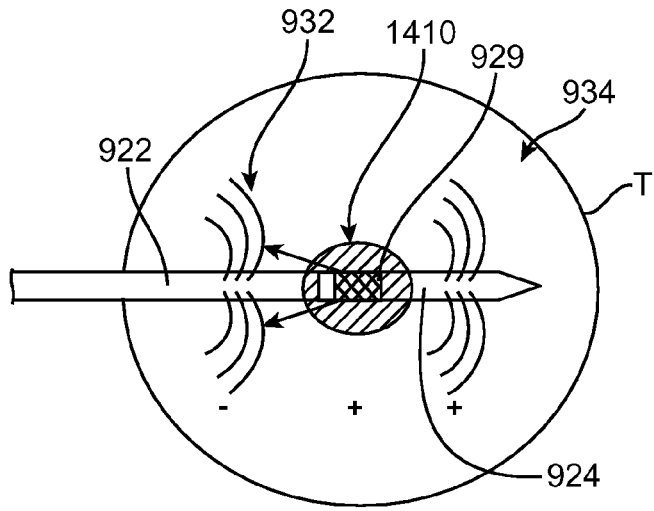
FIG. 14 illustrates formation of an ablation lesion between proximal and distal arrays according to one embodiment.
Figure 15:
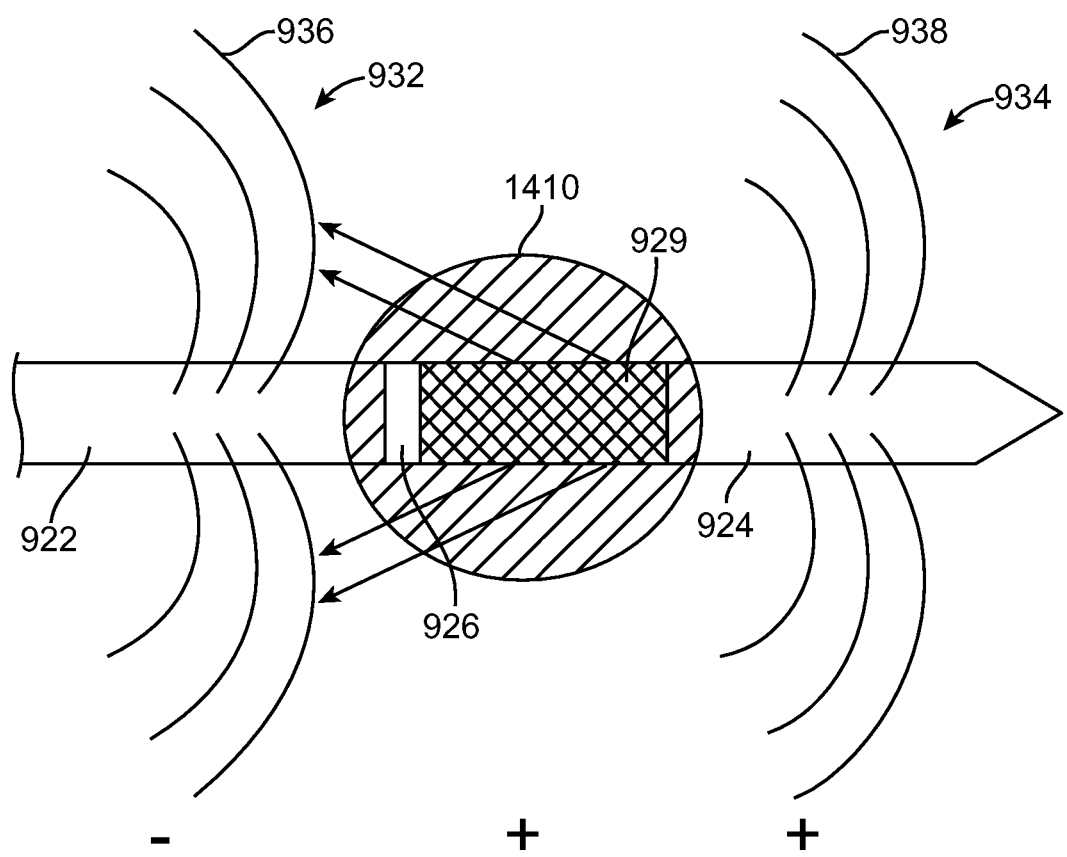
FIG. 15 further illustrates formation of an ablation lesion as illustrated in FIG. 14.

Referring to FIGS. 14 and 15, a source of electrical current, such as a RF generator, is connected to the probe 900 and operated to create a three-dimensional lesion or ablation region 1410 within the diseased tissue (T). As shown in FIGS. 14 and 15, the lesion 1410 is formed in a "middle" region between the proximal and distal electrode arrays 932 and 934. In the illustrated embodiment, the middle lesion 1410 is initially formed adjacent to the exposed, conductive outer surface 929 of the distal cannula 924.

Figure 16:
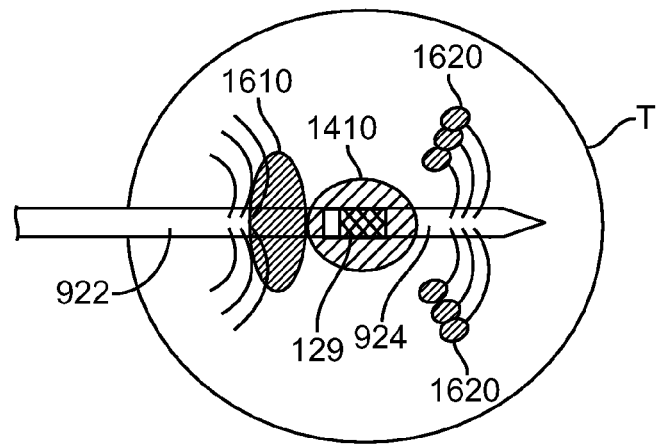
FIG. 16 illustrates growth of an ablation lesion between proximal and distal arrays and formation of ablation lesions around the proximal and distal arrays according to one embodiment.
Figure 17:
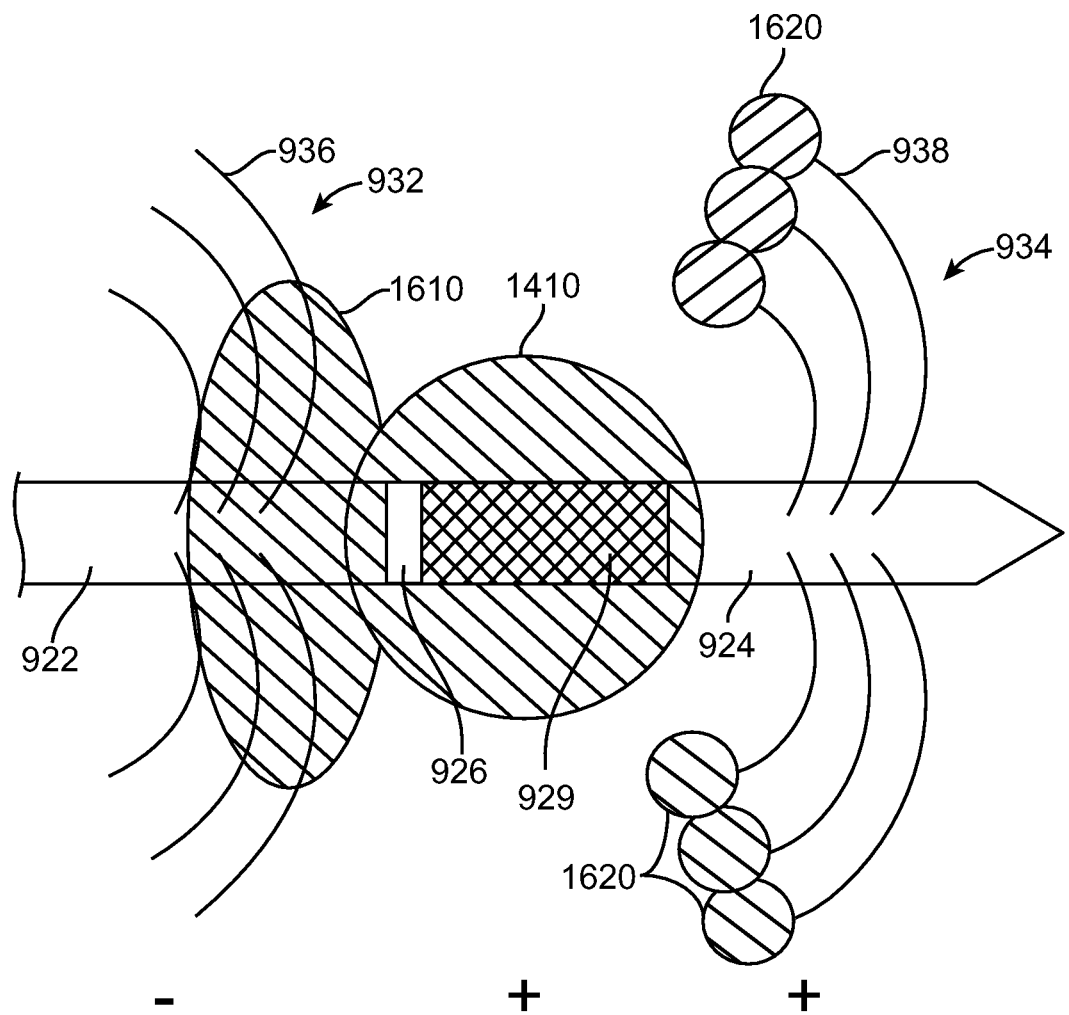
FIG. 17 further illustrates growth and formation of ablation lesions as illustrated in FIG. 16.

Referring to FIGS. 16 and 17, as additional current is applied to the probe 900, the middle lesion 1410 grows, and additional ablation regions 1610 and 1620 develop around respective proximal and distal electrode arrays 932 and 934. More particularly, an elongated lesion 1610 forms around the individual electrodes 936 of the proximal electrode array 922, and multiple smaller lesions 1620 develop around distal tips of electrodes of the distal electrode array.

Figure 18:
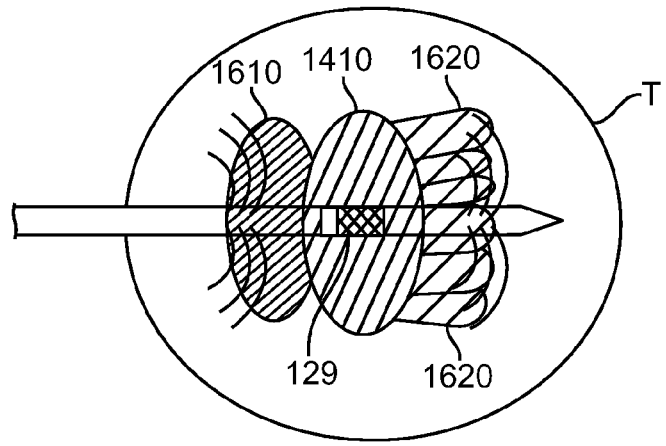
FIG. 18 illustrates further growth of an ablation lesion between proximal and distal arrays and growth of ablation lesions around the proximal and distal arrays according to one embodiment.
Figure 19:
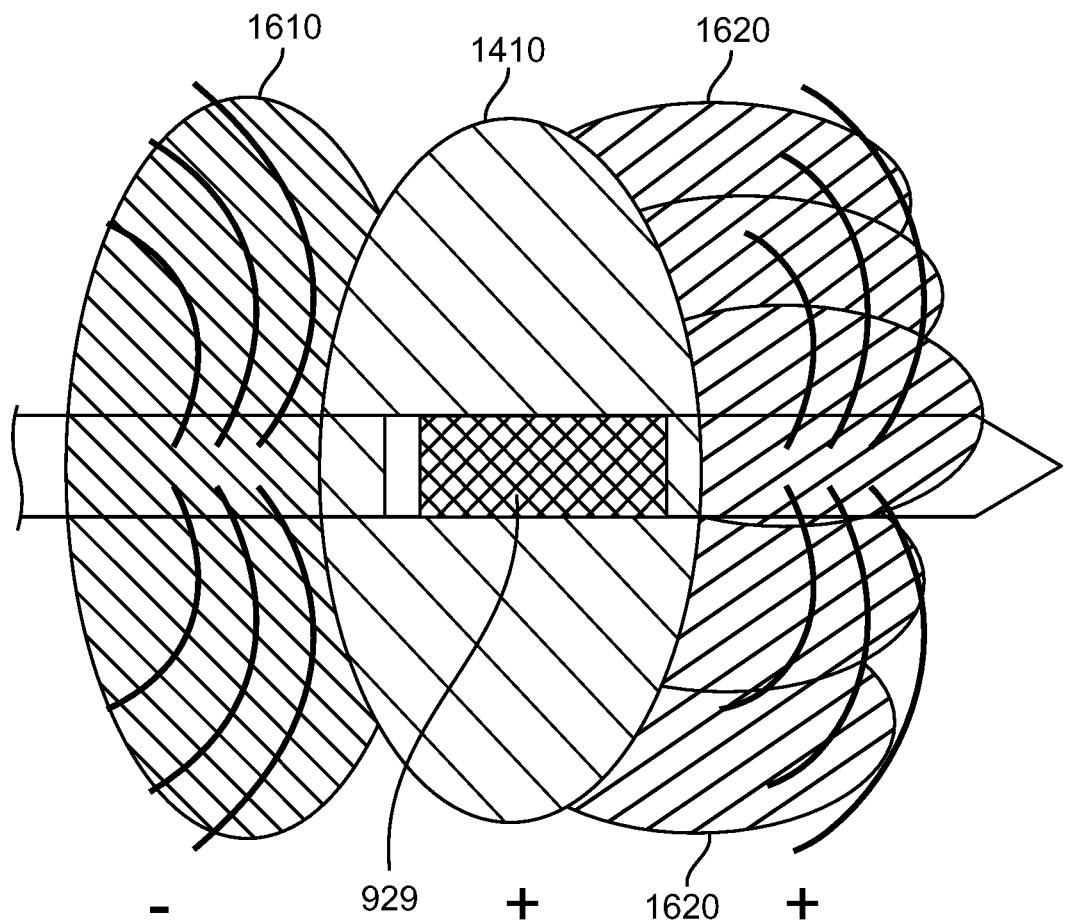
FIG. 19 further illustrates growth of ablation lesions as illustrated in FIG. 18.
Figure 20:
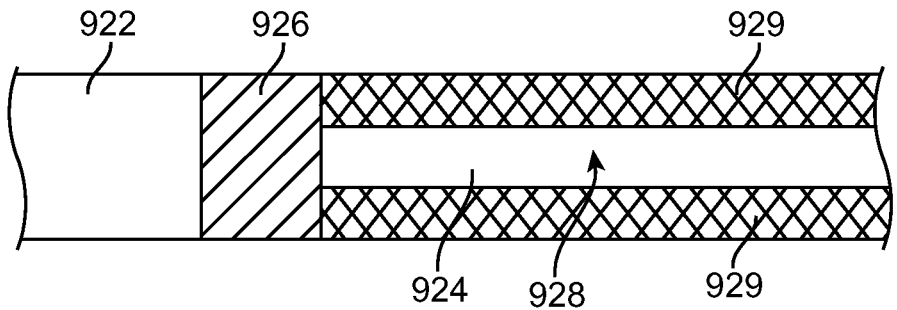
FIG. 20 illustrates an uninsulated, conductive outer surface of a shaft according to one embodiment.

Referring to FIGS. 18 and 19, as additional current is applied to the probe 900, the middle lesion 1410, the elongated lesion 1610, and lesions 1620 expand and grow to so that a lesion is formed "inside-out" and the diseased tissue T is treated.

Thus, embodiments advantageously initiate ablation in a middle region between the proximal and distal electrode arrays 932 and 934, and ablation expands outwardly towards the electrode arrays 932 and 934 in an "inside out" manner. Embodiments, therefore, enhance ablation of diseased tissue by providing more effective spherical and complete ablation lesions without having to wait for ablation around the distal electrode array 934 to "catch up" to the ablation region around the proximal electrode array 932 or for ablation to eventually migrate to middle regions between the arrays 932 and 934, thus preventing the formation of hourglass shaped ablation lesions.

Figure 21:
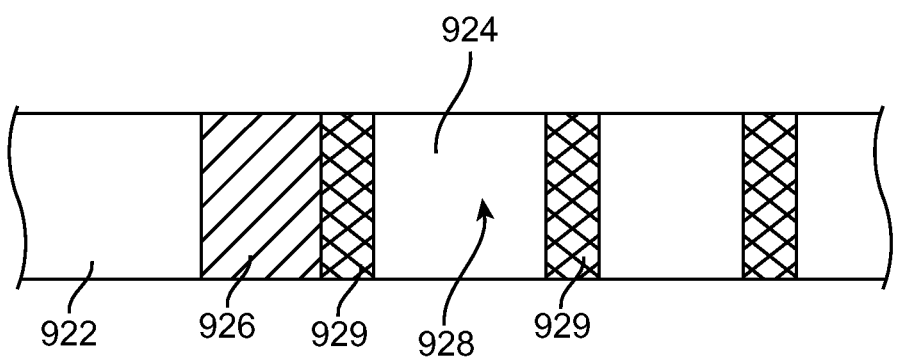
FIG. 21 illustrates an uninsulated, conductive outer surface of a shaft according to another embodiment.
Figure 22:
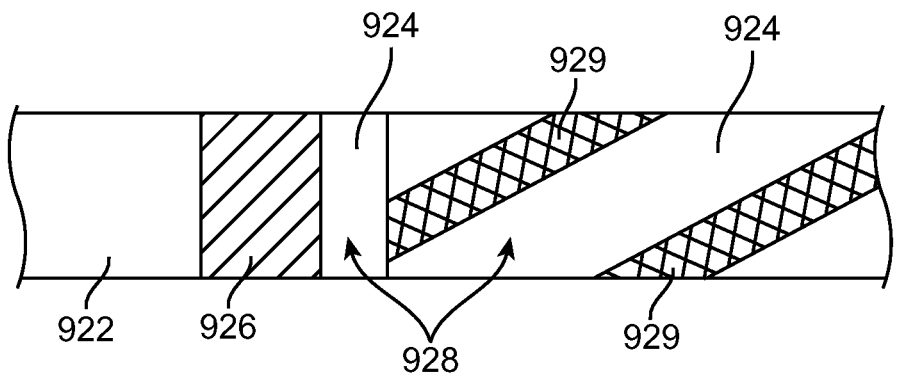
FIG. 22 illustrates an uninsulated, conductive outer surface of a shaft according to a further embodiment.

Further, although various figures illustrate a single uninsulated region 929 that extends circumferentially around a distal cannula 924, alternative embodiments can include different numbers, arrangements, patterns, and shapes of uninsulated regions or surfaces 929. For example, referring to FIG. 20, according to another embodiment, a probe 900 can include one or more uninsulated regions 929 that extend axially along a length of the distal cannula 924. FIG. 21 also illustrates that a section of the distal cannula 924 having an insulated coating 928 can be between uninsulated regions 929. Further, referring to FIG. 22, a distal cannula 924 can include multiple uninsulated surfaces or regions 929. FIG. 21 also illustrates that an uninsulated region 929 can be adjacent to the insulated member 926 or may be between two sections that include an insulative coating 928. Further, rather than strips or rings, embodiments can include discrete uninsulated elements 929, such as dots. Referring to FIG. 22, in a further alternative embodiment, a distal cannula 924 can include strips of uninsulated regions 929 that spiral around the distal cannula 924. Thus, in the illustrated embodiment, there are one or more strips that include an insulative coating 928 and one or more stripes of uninsulated, exposed and conductive outer surfaces 929.

As shown in the various figures, alternative embodiments can include different numbers, shapes, arrangements, patterns, lengths, widths and locations of uninsulated, exposed outer surfaces 929 and sections having an insulative coating 928 and in order to advantageously customize ablation formation and growth of middle ablation lesions 1410 to suit particular probe configurations and surgical needs.

Figure 23:
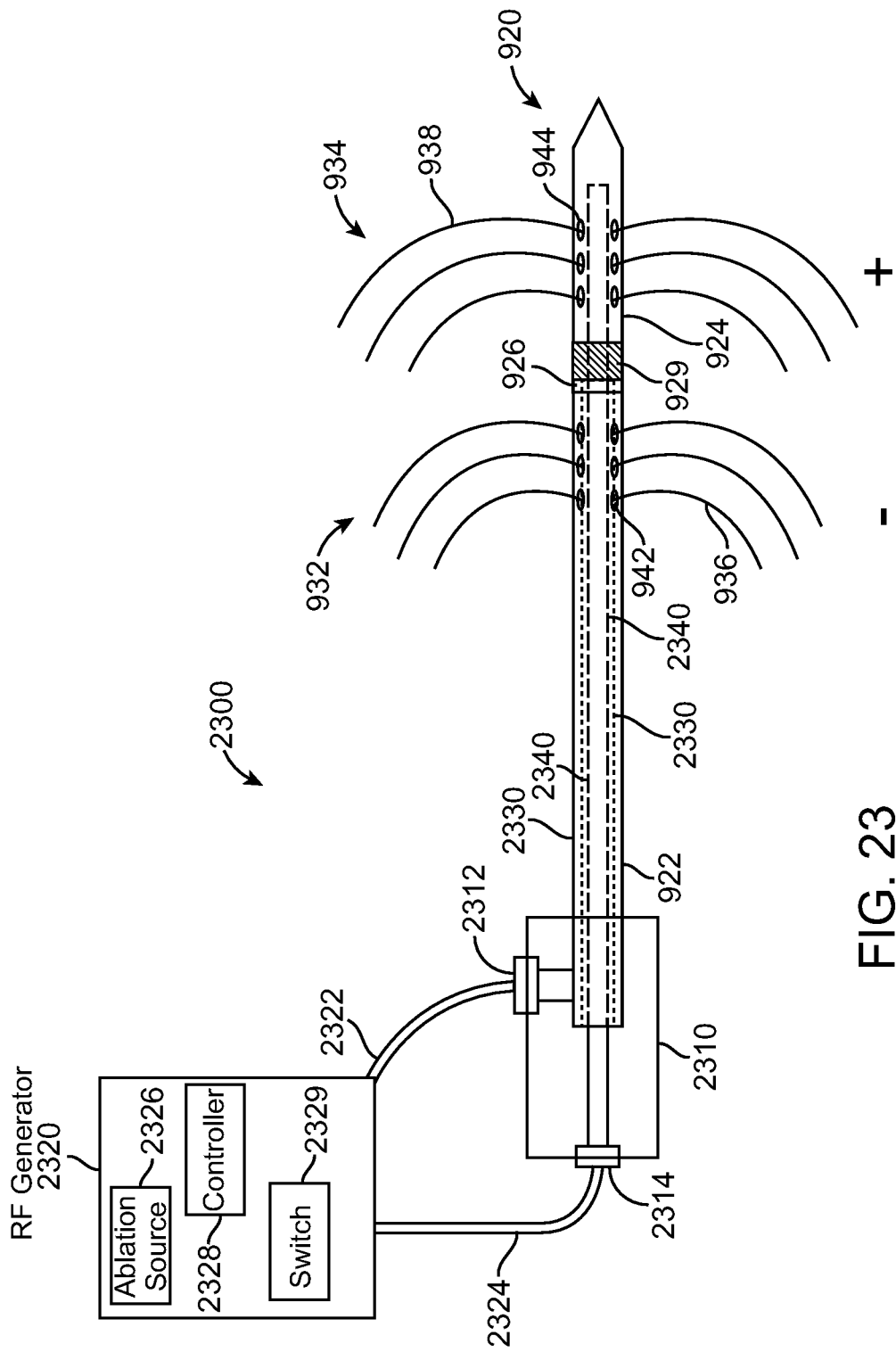
FIG. 23 illustrates a tissue ablation system constructed in accordance with one embodiment.

FIG. 23 illustrates a probe assembly 2300 embodiment and one manner in which electrical current can be applied to the probe assembly 2300. A probe assembly 2300 according to one embodiment includes a shaft 920 that includes a proximal electrode or cannula 922, a distal electrode or cannula 924, an insulative member 926 positioned between the distal end of the proximal cannula 922 and the proximal end of the distal cannula 924 to electrically isolate the cannulas 922 and 924. A handle 2310 receives or is connected to a proximal end of the shaft 920. In the illustrated embodiment, the handle 2310 includes a first connector or interface 2312 for connecting a first lead 2322 of a current source, such as a RF generator 2320, to the probe 2300, and a second connector or interface 2314 for connecting a second lead 2324 of the RF generator 2320 to the probe 2300. In the illustrated example, one connector 2312 is located on a side of the handle 2310, and another connector 2314 is located at a proximal end of the handle 2310, but other configurations can also be utilized.

The RF generator 2320 is configured to supply RF energy to the probe assembly 2300 in a controlled manner. The RF generator 2320 can be a conventional RF power supply that operates at a frequency in the range from 200 KHz to 1.25 MHz, with a conventional sinusoidal or non-sinusoidal wave form. Suitable RF generators 2320 that can be used with embodiments are available from commercial vendors, such as Boston Scientific Corporation of San Jose, Calif., which markets these power supplies under the trademarks RF 2000® (100 W) and RF 3000®. (200 W).

One suitable RF generator 2320 includes a RF ablation source 2326, a controller 2328, and a switch 2329. The controller 2328 is configured to control the switch 2329 in order to simultaneously or sequentially provide RF energy from the ablation source 2326 to the probe, i.e., to the proximal array shaft 2330 seated within the shaft or cannula 920 and the distal array shaft or mandrel 2340, seated within the proximal array shaft 2330, to which respective proximal and distal electrode arrays 932 and 934 are attached. Further aspects of ablation system components and providing electrical current to electrode arrays 932 and 934 are provided in U.S. Publication No. 2005/00800409 A1, the contents of which were previously incorporated herein by reference as though set forth in full.

In the illustrated embodiment, the negative lead 2322 is electrically connected to a proximal array shaft 2330 carried by the shaft 920 via connector 2312. The proximal electrode array 932 is coupled to the proximal array shaft 2330. Electrodes 936 of the proximal electrode array 932 are deployed through apertures or ports 942 defined by the outer shaft 920. Similarly, the positive lead 2324 is electrically connected to a distal array proximal shaft or mandrel 2340 via connector 2314. The proximal array shaft 2330 and the distal array shaft 2340 are electrically insulated from each other. In the illustrated embodiment, the distal array proximal shaft 2340 extends through a lumen defined by the proximal array shaft 2330 and through the insulative member 926. Electrodes 938 of the distal electrode array 934 are deployed through apertures or ports 944 defined by the outer shaft 920.

For example, the shaft 920 comprises a proximal cannula 922 having a reciprocating proximal array shaft 2330 to which the proximal electrode array 932 is attached, and a reciprocating distal shaft or mandrel 2340 to which a distal electrode array 934 is attached. Each electrode array 932 and 934 includes a plurality of tissue penetrating needle electrodes 934 and 938 suitably mounted to respective shafts 2330 and 2340. Longitudinal translation of a proximal or distal shaft 2330 or 2340 deploys the electrode arrays 932 and 934, and translation in the opposite direction retracts the electrode arrays 932 and 934 into respective cannulas 922 and 924. The distal ends of the needle electrodes 936 and 938, when retracted, reside within the ports defined by respective cannulas 922 and 924 in order to facilitate movement of the electrodes during deployment.

In the illustrated embodiment, each individual electrode 936 and 938 is in the form of small diameter metal element such as a needle that can penetrate into tissue when deployed. The needle electrodes 936 and 938 are resilient and pre-shaped to assume a desired configuration when advanced into tissue. When deployed from a cannula, each electrode array 932 and 934 is placed in a three-dimensional configuration that defines a generally ellipsoidal or spherical volume. For example, the resulting volume can have a periphery with a maximum radius in the range from 0.5 to 4 cm. The needle electrodes 936 and 938 are curved and diverge radially outwardly from the cannulas 922 and 924 in a uniform pattern, i.e., with the spacing between adjacent needle electrodes 936 and 938 diverging in a substantially uniform and/or symmetric pattern. Other embodiments may involve non-uniform and staggered patterns. For ease of explanation, reference is made to patterns illustrated in the figures.

In the illustrated embodiment, the needle electrodes 936 and 938 of respective electrode arrays 932 and 934 evert from respective cannulas 922 and 924 and face the same direction, i.e., they are arranged to provide an asymmetric probe configuration. Further aspects of suitable electrode arrays, needles, and manner of deploying and retracting the arrays are described in U.S. Application Publication No. 2005/0080409, the contents of which were previously incorporated herein by reference. It will be appreciated that various numbers and configurations of arrays and electrodes and different deployment mechanisms can be utilized.

Embodiments can be implemented in probes having various insulative configurations, e.g. to provide bipolar modality. In one embodiment, proximal and distal cannulas 922 and 924 are separated by an insulative member 926 (as shown in FIG. 10). The insulative member 926 can be connected to the ends of the proximal and distal cannulas 922 or 924 or molded to connect the ends, e.g., using injection or micro-molding.

Figure 24:
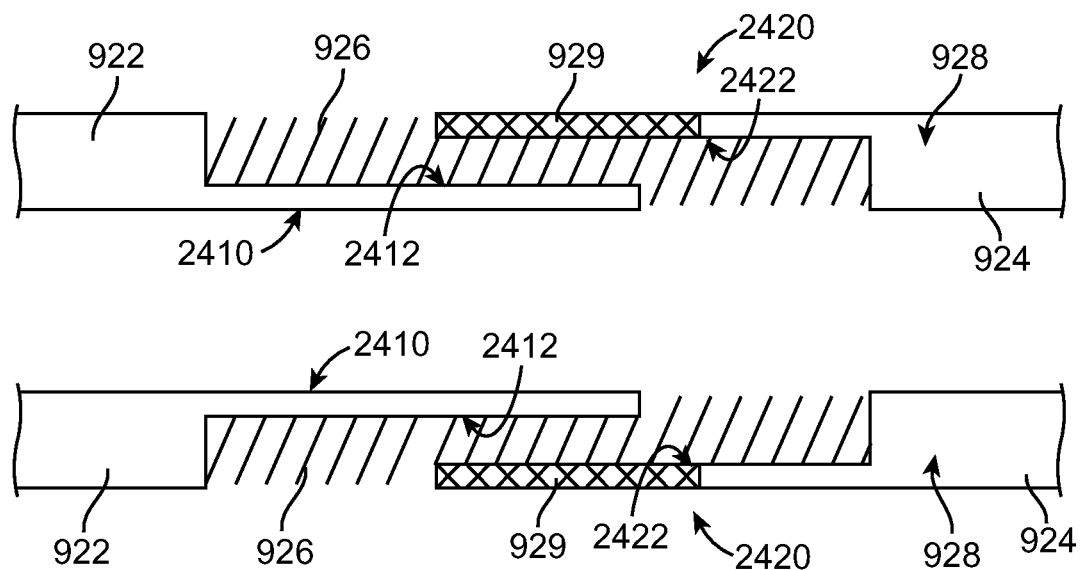
FIG. 24 is a partial cross-sectional view of an ablation probe according to one embodiment having an end with a reduced diameter and an end with an enlarged inner diameter and an uninsulated, conductive outer surface.
Figure 25:
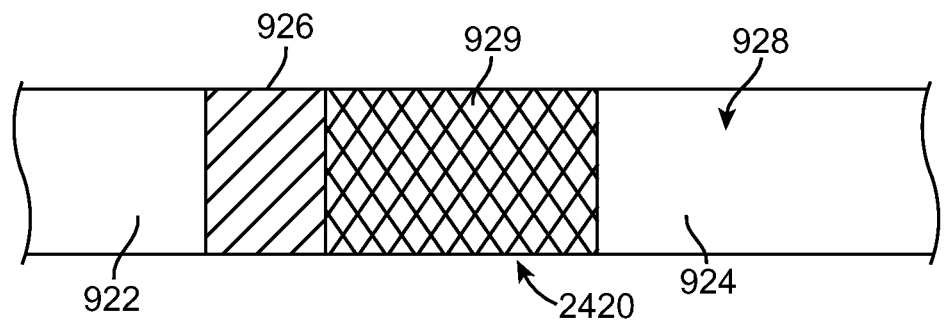
FIG. 25 is a top view of FIG. 24.
Figure 26:
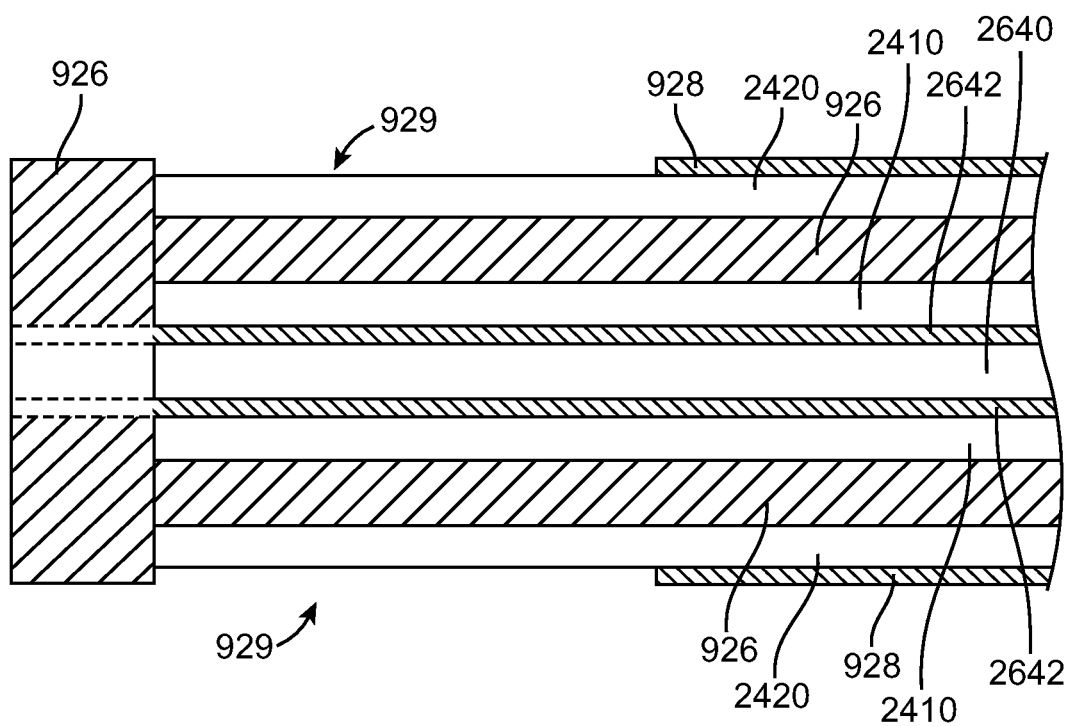
FIG. 26 further illustrates overlapping ends of cannulas of an ablation probe having an uninsulated outer surface according to one embodiment.

Referring to FIG. 24-26, in another embodiment, a distal end of the proximal cannula 922 and the proximal end of the distal cannula 924 can be configured so that they overlap and are separated by the insulative member 926. In the illustrated example, a distal end of a proximal cannula 922 can be an end 2410 having a reduced outer diameter. A reduced outer diameter end can, for example, be made by removing or machining an outer surface of the distal end of the proximal cannula 922. As shown in FIG. 24, the inner diameter of the distal end 2410 remains the same. Additionally, a proximal end of a distal cannula 924 can be a bored end 2620 having an enlarged inner diameter that can, for example, be made by removing or machining an inner surface of the proximal end of the distal cannula 924. As shown in FIG. 26, a distal shaft or mandrel 2640 that carries the distal electrode array 938 extends through the insulative member 926 and includes an insulative coating 2642. Thus, the distal mandrel 2640 is electrically insulated from the distal end of the proximal cannula 922 having a reduced outer diameter.

The insulative member 926 can be inserted or injected into the space between the ends of the proximal and distal cannulas 922 and 924 and, in addition, into the space between an inner surface 2422 of the bored end 2420 of the distal cannula 924 and an outer surface 2412 of the end 2410 of the proximal cannula 922 having a reduced outer diameter. In this manner, insulative material 926 extends laterally into portions of the shaft 920 between the proximal and distal cannulas 924 to provide enhanced strength and support to the probe. Additional aspects of overlapping insulated proximal and distal cannulas or electrodes 922 and 924 are provided in Provisional Application No. 60/985,201, filed on Nov. 3, 2007 and entitled "Bipolar Electrosurgical Probe Having Insulated Overlapping Conductive Elements", the contents of which are incorporated herein by reference. Persons skilled in the art will appreciate that various other probe configurations can be utilized, and that FIGS. 24-26 illustrate one example of how a probe can be configured.

Figure 27:
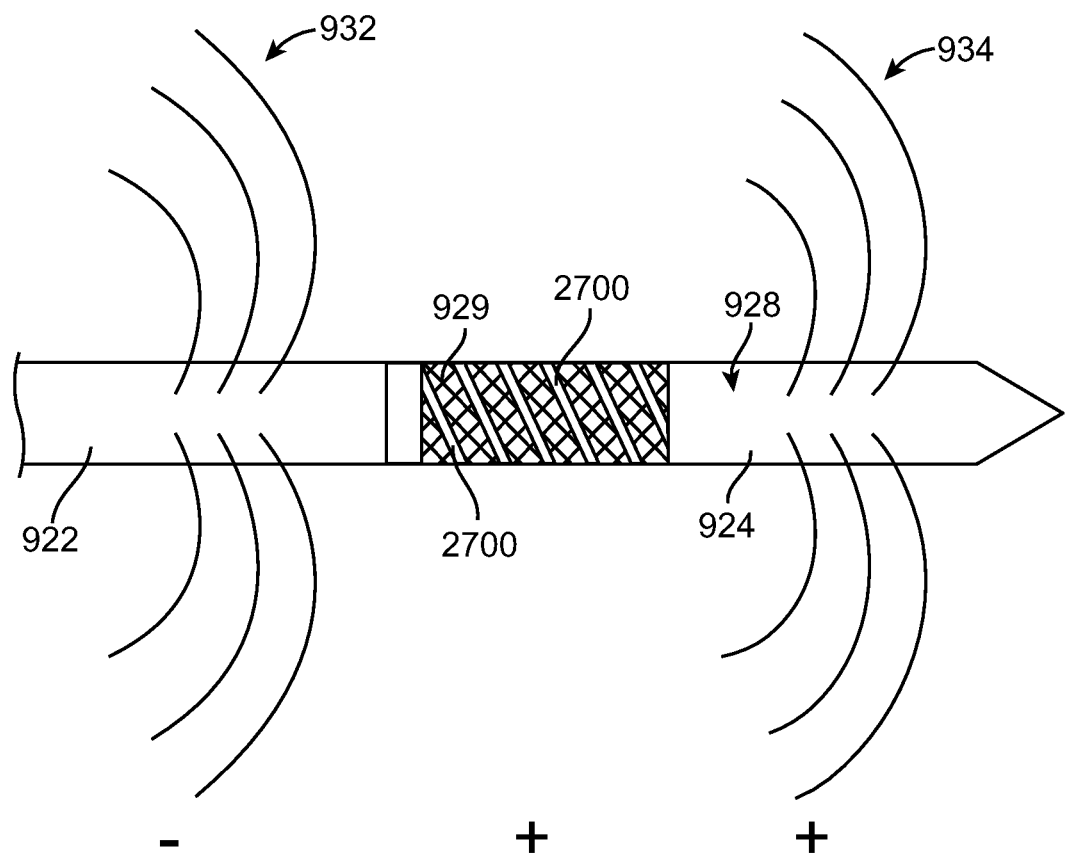
FIG. 27 illustrates an uninsulated outer surface of a shaft of an ablation probe having one or more current enhancing protrusions according to another embodiment.
Figure 28:
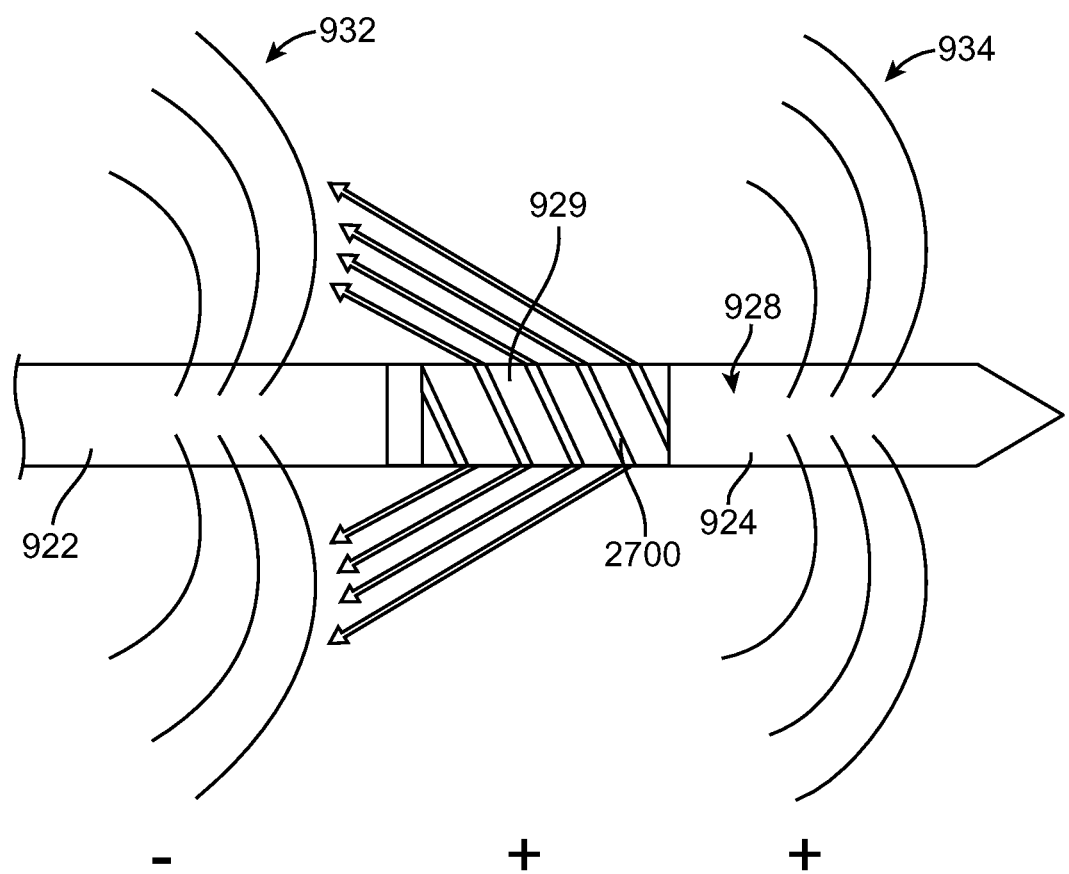
FIG. 28 illustrates how the one or more protrusions increase current density according to one embodiment.
Figure 29:
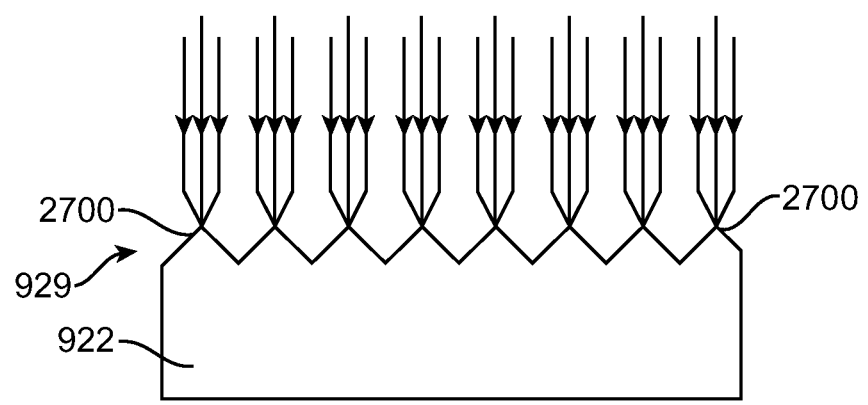
FIG. 29 generally illustrates enhanced current density resulting from an uninsulated outer surface of a shaft having current enhancing protrusions according to on embodiment.
Figure 30:
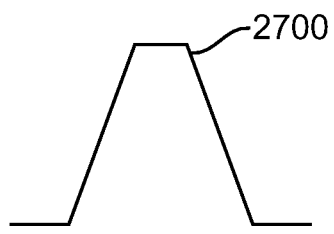
FIG. 30 illustrates a current enhancing protrusion in the form of a ridge according to one embodiment.

Referring to FIGS. 27-29, according to another embodiment, an uninsulated, electrically conductive outer surface 929 of the distal cannula 924 can include one or more current enhancing protrusions 2700 that extend upwardly or outwardly from the outer surface 929, e.g., upwardly or outwardly relative to a central axis defined by the probe, e.g. a central axis defined by the shaft 920. The current enhancing protrusions 2700 concentrate electrical current and increase current density (generally illustrated by double arrows in FIG. 28 and converging arrows in FIG. 29) along the shaft 920 between the proximal and distal electrode arrays 932 and 934. The protrusions 2700 can enhance ablation in the region adjacent to the protrusions 2700, e.g., in a middle region of a diseased tissue between electrode arrays 932 and 934.

As shown in FIGS. 27 and 28, the distal electrode array 934 and the uninsulated outer surface 929 and protrusions 2700 extending from the outer surface 929 are the same polarity. In the illustrated embodiment, the uninsulated outer surface 929, protrusions 2700 and distal electrode array 934 have a positive (+) polarity, and the proximal electrode array 932 has a negative (−) polarity.

Figure 31:
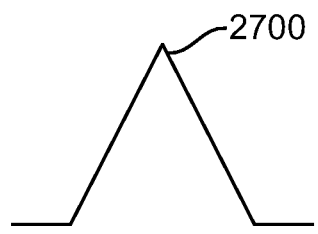
FIG. 31 illustrates a current enhancing protrusion in the form of an edge or a point according to another embodiment.
Figure 35A:
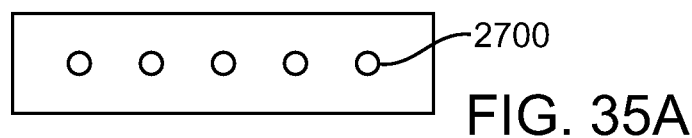
FIG. 35A is a top view of an uninsulated outer surface of a shaft having a plurality of protrusions in the form of dots or columns according to another embodiment.
Figure 35B:
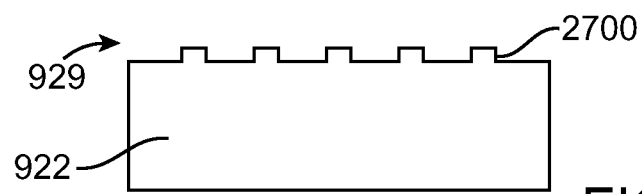
FIG. 35B is a side view of FIG. 35A.

Embodiments can include various numbers, shapes, patterns and sizes of protrusions 2700 depending on, for example, the desired ablation biasing and concentration needs. For example, a protrusion 2700 can be in the form of a ridge (FIG. 30) which includes a top portion that does not terminate at a point. In an alternative embodiment, a protrusion 2700 can be in the form of a point or edge (FIG. 31). For example, a protrusion 2700 may be in the form of a cone or a have a triangle-shaped cross section. While greater current densities can be achieved with protrusions 2700 having smaller dimensions (pointed protrusion), embodiments can also be implemented using current enhancing protrusions 2700 that increase current densities to a lesser degree using non-pointed current enhancing protrusions 2700

Figure 36A:
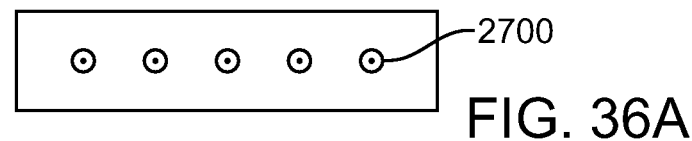
FIG. 36A is a top view of an uninsulated outer surface of a shaft having a plurality of protrusions in the form of conical or pointed members according to a further embodiment.
Figure 36B:
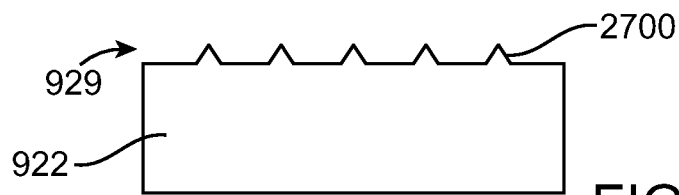
FIG. 36B is a side view of FIG. 36A.
Figure 37A:
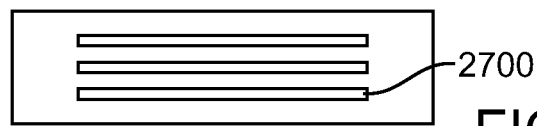
FIG. 37A is a top view of an uninsulated outer surface of a shaft having a plurality of protrusions in the form of lateral ridges or edges extending along a length of the uninsulated outer surface according to another embodiment.
Figure 37B:
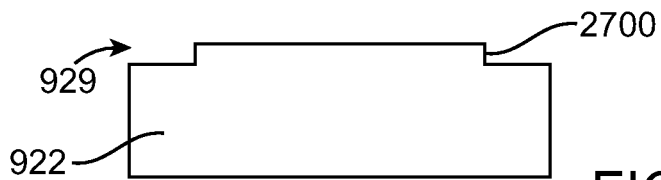
FIG. 37B is a side view of FIG. 37A.
Figure 38A:
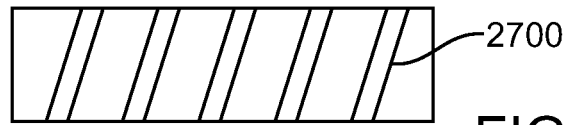
FIG. 38A is a top view of an uninsulated outer surface of a shaft having a threaded protrusion according to another embodiment.
Figure 38B:
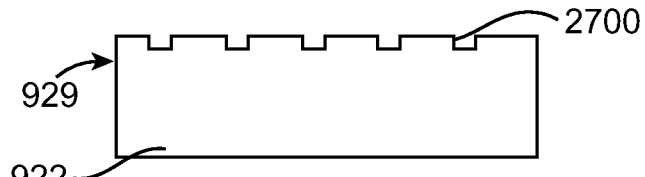
FIG. 38B is a side view of FIG. 38A.
Figure 39A:
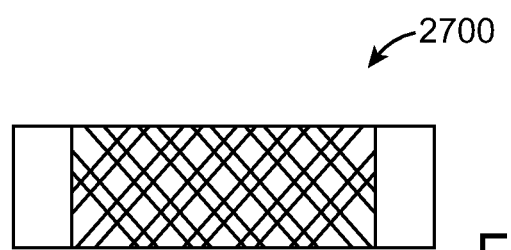
FIG. 39A is a top view of an uninsulated outer surface of a shaft having multiple protrusions extending in different directions according to another embodiment.
Figure 39B:
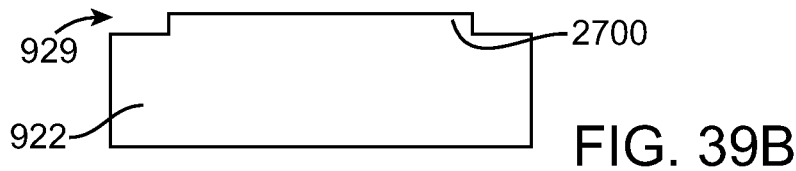
FIG. 39B is a side view of FIG. 39A.

In alternative embodiments, a protrusion 2700 can be in the form of a raised rectangular member (FIGS. 32A and 32B), a raised triangular member having a pointed tip (FIGS. 33A and 33B), or a raised rounded member (FIGS. 34A and 34B), raised dots, columns or discrete protrusions (FIGS. 35A and 35B) or raised conical protrusions (FIGS. 36A and 36B). In certain embodiments, the protrusions 2700 extend around an uninsulated outer surface 929. In other embodiments, the protrusion 2700 can extend laterally along a length of the uninsulated outer surface 929 (FIGS. 37A and 37B). Further, the protrusion 2700 can be a threaded element (FIGS. 27, 38A and 38B). A shaft 920 can also include a plurality of different individual protrusions 2700 arranged in various patterns (FIGS. 39A and 39B).

Thus, embodiments can include various shapes, sizes, numbers, patterns and arrangements of protrusions 3000 that increase current concentrations in order to bias or enhanced formation of tissue lesions in a customized manner as needed. In embodiments in which the protrusions 3000 are formed in or applied or attached to the uninsulated outer surface 929, the protrusions 3000 can enhance formation of an ablation lesion 1410 in a middle region of the tissue between the proximal and distal electrode arrays 932 and 934.

Figure 40:
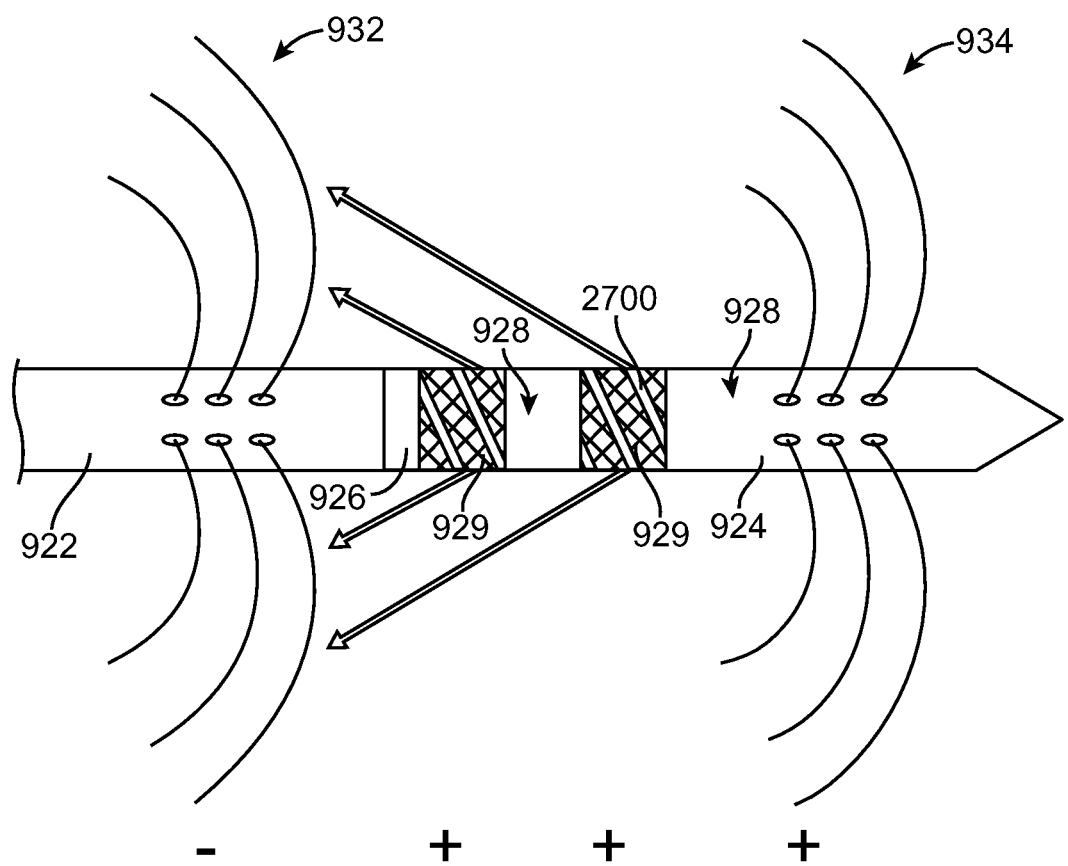
FIG. 40 illustrates an ablation probe having a shaft including multiple uninsulated outer surfaces and current enhancing protrusions according to a further alternative embodiment.

Further, referring to FIG. 40, current enhancing protrusions 2700 can be formed in, defined by, or applied or attached to various numbers of uninsulated outer surfaces or regions 929. In the illustrated embodiment, a distal cannula 924 includes two uninsulated regions 929, and protrusions 2700 can, if necessary, be formed in, defined by, or applied or attached to one or both of the uninsulated regions 929 or other numbers of uninsulated regions 929 as needed. The uninsulated outer surfaces or regions 929 and protrusions 2700 are electrically connected to and the same polarity as the distal electrode array 934. The uninsulated outer surfaces or regions 929 can have various numbers, types, shapes and sizes of protrusions 2700. FIG. 40 illustrates current enhancing protrusions 2700 in the context of multiple uninsulated surfaces 929, but embodiments can also be implemented so that a single uninsulated surface 929 (e.g., as shown in FIGS. 10 and 11) include one or more current enhancing protrusions 2700.

Figure 41:
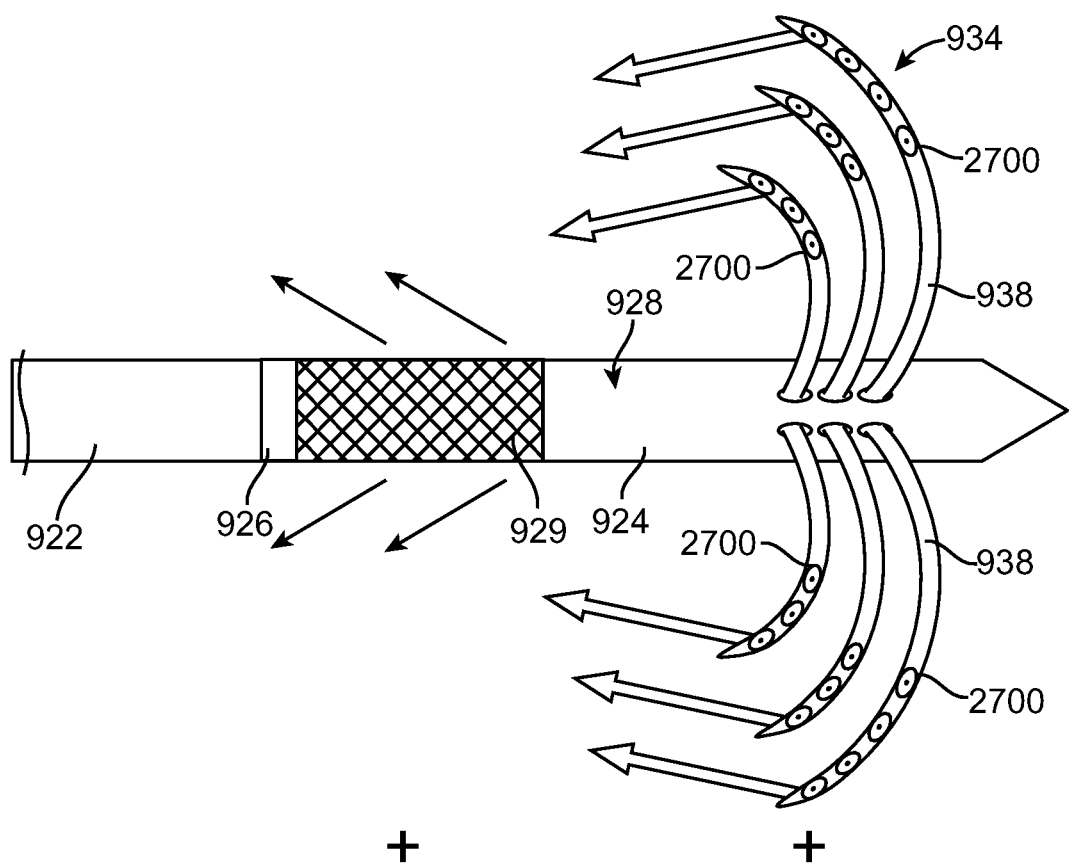
FIG. 41 illustrates an ablation probe having a shaft including an uninsulated outer surface and electrodes extending through apertures defined by the shaft including one or more current enhancing protrusions according to another embodiment.

In a further alternative embodiment, referring to FIG. 41, one or more current enhancing protrusions 2700 can be formed in or applied or attached to individual electrodes of an electrode array. For example, in the illustrated embodiment, electrodes 938 of a distal electrode array 934 include multiple protrusions 2700 (in the form of a cone as shown in FIGS. 36A and 36B)) in order to increase current density at the electrodes 938 and enhance formation of ablation lesions 1610 and/or 1620 around the electrodes 938. One or more or all of the electrodes 938 can have one or more protrusions 2700 of various types, shapes and sizes in order to increase the current density around these conductive surfaces.

Figure 42:
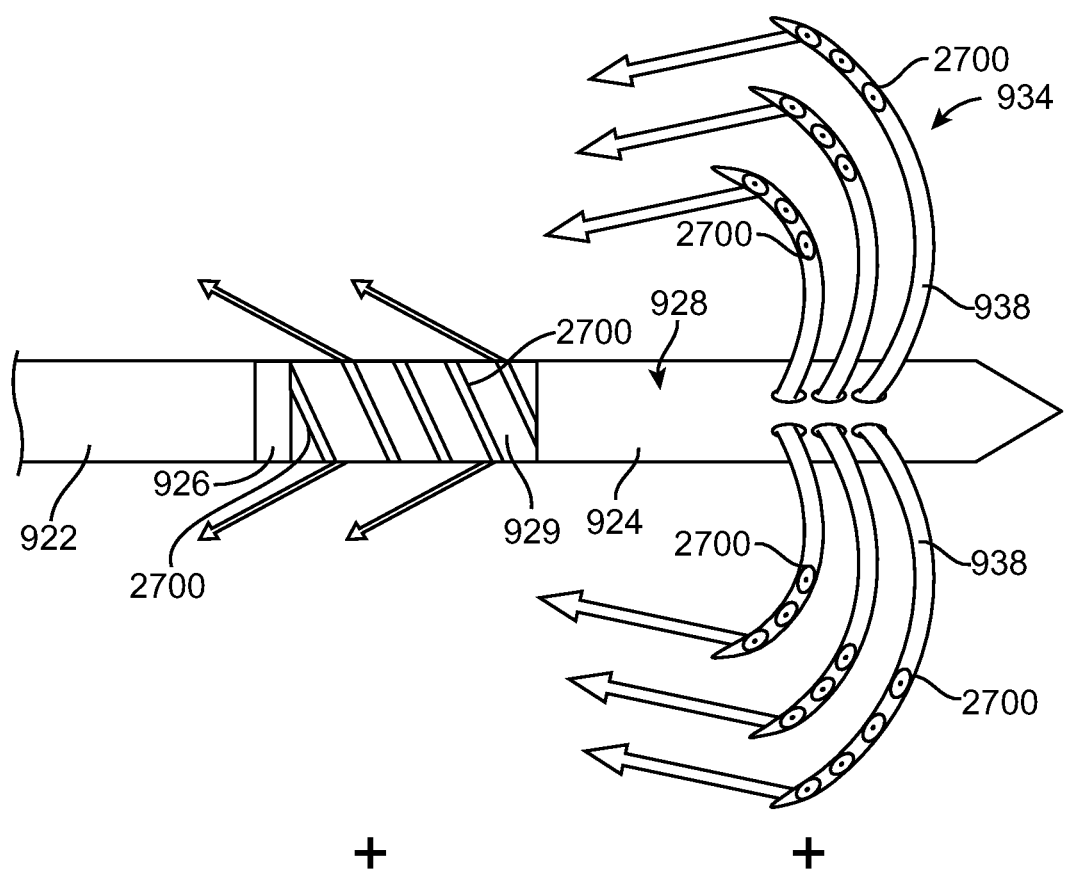
FIG. 42 illustrates an ablation probe having a distal cannula including an uninsulated outer surface and one or more current enhancing protrusions, and electrodes extending through apertures defined by the distal cannula and also including one or more current enhancing protrusions according to another alternative embodiment.

In another alternative embodiment, referring to FIG. 42, one or more protrusions 2700 can be formed in or applied or attached to one or more or all of the uninsulated regions or outer surfaces 929 of the distal cannula 924 (as shown in FIG. 28) and, in addition, one or more protrusions 2700 can be formed in or applied or attached to one or more or all of the electrodes of an electrode array. In the illustrated embodiment, a current enhancing protrusion 2700 in the form of a threaded element extends around the uninsulated outer surface 929 of the distal cannula 924, and electrodes 938 of the distal electrode array 934 include cone-shaped protrusions 2700. One or more or all of the uninsulated surfaces or regions 929 and one or more or all of the electrodes of an electrode array can include various numbers, types and sizes of protrusions 2700 in order to increase the current density around these conductive surfaces.

Although particular embodiments have been shown and described, it should be understood that the above description is not intended to limit the scope of embodiments since various changes and modifications may be made without departing from the scope of the claims. For example, although the figures illustrates embodiments in the context of conductive elements in the form of asymmetric arrays in which the electrode arrays face the same direction, embodiments can also be implemented in probes having conductive elements in the form of symmetric arrays in which the electrode arrays face each other. As a further example, a portion of a distal cannula or a portion of the proximal cannula can be uninsulated in order to facilitate ablation of a middle portion of a diseased tissue or reduce ablation times. Further, embodiments including current enhancing protrusions can be applied to various probes and can be used with monopolar and bipolar probes. Moreover, in certain embodiments, an uninsulated outer surface is electrically connected to a first conductive element or electrode array, and the outer surface and the first conductive element or electrode array are electrically insulated from a second electrode array. Further, current enhancing protrusions can be applied to probes in which the uninsulated outer surface is electrically insulated from both of the conductive elements or electrode arrays. Moreover, current enhancing protrusions can be used with bipolar and monopolar probes. Additionally, although certain embodiments are described in the context of two electrode arrays, embodiments can also be applied to probe assemblies having no electrode arrays, one electrode arrays, or more than two electrode arrays.

Accordingly, although particular embodiments have been shown and described, it should be understood that the various changes and modifications may be made without departing from the scope of the claims.

What is claimed is:

1. A tissue ablation probe comprising:
    a proximal electrode array comprising a first plurality of electrodes;
    a distal electrode array comprising a second plurality of electrodes; and
    a shaft carrying the proximal and distal electrode arrays, the shaft comprising a proximal cannula having a plurality of apertures dimensioned for passage of the proximal electrode array and a distal cannula having a plurality of apertures dimensioned for passage of the distal electrode array, the proximal cannula and the distal cannula being electrically isolated from one another by an insulating member, wherein the distal cannula has an uninsulated outer surface located between the apertures of the proximal cannula and the apertures of the distal cannula, the uninsulated outer surface being electrically connected to the distal electrode array, and the uninsulated outer surface and the distal electrode array are insulated from the proximal electrode array,
    wherein the uninsulated outer surface is exposed during ablation, such that electrical current initially flows between the uninsulated outer surface and the proximal electrode array during ablation to initially form a lesion adjacent to the uninsulated outer surface.

2. The tissue ablation probe of claim 1, further comprising an inner shaft contained in the proximal cannula and the distal cannula and coupled to the distal array, the inner shaft being electrically coupled to the uninsulated outer surface.

3. The tissue ablation probe of claim 1, wherein the uninsulated outer surface and the distal electrode array are the same polarity when electrical current is conveyed to the probe.

4. The tissue ablation probe of claim 1, wherein the proximal and distal electrode arrays face the same direction.

5. The tissue ablation probe of claim 3, wherein the uninsulated outer surface and the distal electrode array have a positive polarity.

6. The tissue ablation probe of claim 1, wherein the uninsulated outer surface extends circumferentially around the shaft.

7. The tissue ablation probe of claim 1, wherein the uninsulated outer surface extends axially along a length of the shaft.

8. The tissue ablation probe of claim 1, wherein the uninsulated outer surface comprises multiple uninsulated surfaces.

9. The tissue ablation probe of claim 1, wherein the uninsulated outer surface comprises multiple rings.

10. The tissue ablation probe of claim 1, wherein the uninsulated outer surface comprises one or more spiral stripes around a length of the shaft.

11. The tissue ablation probe of claim 1, wherein the uninsulated outer surface comprises one or more current enhancing protrusions.

12. The tissue ablation probe of claim 11, wherein the current enhancing protrusion comprises a ridge including a top portion that does not terminate in a point.

13. The tissue ablation probe of claim 11, wherein the current enhancing protrusion has a cone or triangular-shaped cross-section.

14. The tissue ablation probe of claim 2, wherein the inner shaft electrically couples to the uninsulated outer surface when the distal electrode array passes through apertures of the distal cannula.

* * * * *